United States Patent
Ciftlik et al.

(10) Patent No.: US 10,436,683 B2
(45) Date of Patent: Oct. 8, 2019

(54) SAMPLE PROCESSING DEVICE WITH DETACHABLE SLIDE

(71) Applicant: ECOLE POLYTECHNIQUE FEDERALE DE LAUSANNE (EPFL), Lausanne (CH)

(72) Inventors: Ata Tuna Ciftlik, Lausanne (CH); Martin Gijs, Ecublens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 15 days.

(21) Appl. No.: 14/381,084

(22) PCT Filed: Feb. 15, 2013

(86) PCT No.: PCT/IB2013/051245
§ 371 (c)(1),
(2) Date: Aug. 26, 2014

(87) PCT Pub. No.: WO2013/128322
PCT Pub. Date: Sep. 6, 2013

(65) Prior Publication Data
US 2015/0005190 A1    Jan. 1, 2015

(30) Foreign Application Priority Data
Feb. 27, 2012 (CH) .......................... 256/12

(51) Int. Cl.
*B01L 3/00* (2006.01)
*G01N 1/31* (2006.01)
*G01N 33/574* (2006.01)

(52) U.S. Cl.
CPC ............ *G01N 1/312* (2013.01); *B01L 3/5027* (2013.01); *B01L 3/50273* (2013.01);
(Continued)

(58) Field of Classification Search
CPC ......... B01L 2300/0636; B01L 3/50273; B01L 2300/0867; B01L 2300/0822;
(Continued)

(56) References Cited

U.S. PATENT DOCUMENTS

| 8,480,956 B2 | 7/2013 | Kulah et al. |
| 2002/0192701 A1* | 12/2002 | Adey .................. B01F 5/10 |
| | | 435/6.11 |

(Continued)

FOREIGN PATENT DOCUMENTS

| DE | 103 16 723 A1 | 11/2004 |
| EP | 1 974 814 A1 | 10/2008 |

(Continued)

OTHER PUBLICATIONS

International Search Report for PCT/IB2013/051245 dated Aug. 14, 2013.

(Continued)

*Primary Examiner* — Betty J Forman
(74) *Attorney, Agent, or Firm* — Nixon & Vanderhye PC

(57) ABSTRACT

A biological and chemical sample processing device that b. comprises a high pressure-resistant, shallow and wide area microfluidic chamber having at least one wall formed by a detachable slide containing samples such as immobilized entities, biological samples or molecules, c. comprises an arrangement of microfluidic access holes for injecting to and collecting fluid form said chamber, d. is interfaced with inlet ports and microfluidic channels which are formed external to the chamber, e. is configured so that the slide may be brought into contact with the device to form the said chamber, f. is adapted to deliver and to transport fluidic substances and reagents inside said chamber in a fast manner, preferably within less than 15 seconds, and in a regular or uniform way owing to said arrangement of microfluidic access holes.

14 Claims, 13 Drawing Sheets

Figure 1:
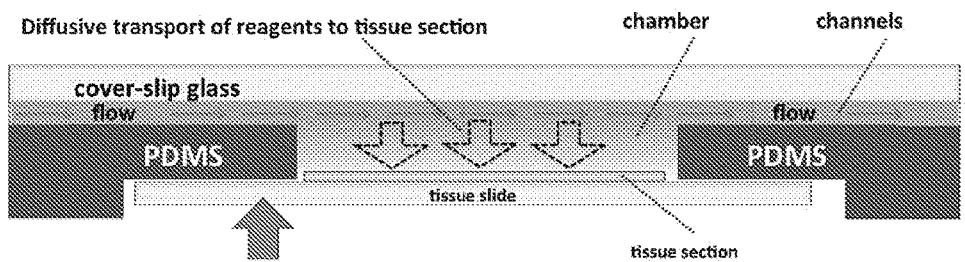

(52) U.S. Cl.
CPC . *G01N 33/57415* (2013.01); *G01N 33/57484* (2013.01); *B01L 2300/0636* (2013.01); *B01L 2300/0819* (2013.01); *B01L 2300/0822* (2013.01); *B01L 2300/0877* (2013.01); *B01L 2300/0887* (2013.01); *B01L 2400/0415* (2013.01); *B01L 2400/0442* (2013.01); *G01N 2333/71* (2013.01); *G01N 2333/723* (2013.01); *G01N 2333/91205* (2013.01)

(58) Field of Classification Search
CPC ........... B01L 2300/0877; B01L 3/5027; G01N 33/54366; G02B 21/34
See application file for complete search history.

(56) References Cited

U.S. PATENT DOCUMENTS

| | | | |
|---|---|---|---|
| 2003/0152927 A1* | 8/2003 | Jakobsen | B01L 3/5027 435/6.16 |
| 2004/0037739 A1* | 2/2004 | McNeely | B01F 5/10 422/417 |
| 2004/0101870 A1* | 5/2004 | Caubet | B01F 11/0071 435/6.12 |
| 2005/0009101 A1 | 1/2005 | Blackburn | |
| 2006/0003440 A1 | 1/2006 | Streit et al. | |
| 2007/0054293 A1* | 3/2007 | Liu | B01F 5/061 435/287.2 |
| 2010/0190265 A1* | 7/2010 | Dufva | B01L 3/5027 436/501 |
| 2011/0240473 A1 | 10/2011 | Kulah et al. | |
| 2012/0312384 A1 | 12/2012 | Robinson et al. | |

FOREIGN PATENT DOCUMENTS

| | | |
|---|---|---|
| WO | 91/07486 A1 | 5/1991 |
| WO | 02/072264 A1 | 9/2002 |
| WO | WO2003015922 | 2/2003 |
| WO | 03/106033 A1 | 12/2003 |
| WO | WO2004050246 | 6/2004 |
| WO | WO2006116037 | 11/2006 |
| WO | 2009029845 | 3/2009 |
| WO | WO2010128483 | 11/2010 |
| WO | 2010/148252 A1 | 12/2010 |
| WO | WO2011026136 | 3/2011 |
| WO | 2011/102801 A1 | 8/2011 |

OTHER PUBLICATIONS

Written Opinion of the International Searching Authority for PCT/IB2013/051245 dated Aug. 14, 2013.
Search Report for CH 00256/12 dated Jun. 12, 2012.
A. Ciftlik et al., "Fast Imminohistochemical Biomarker Detection Device for Cancer Tissue Slices", 14$^{th}$ International Conference on Miniaturized Systems for Chemistry and Life Sciences, Oct. 3-7, 2010, pp. 699-701.
"Breast Cancer Diagnosis Using a Microfluidic Multiplexed Immunohistochemistry Platform," Kim et al, May 2010, vol. 5, Issue 5, PLos ONE.
"Determining the optimal PDMS—PDMS bonding technique for microfluidic devices," *Journal of Micromechanics and Microengineering*, Eddings et al, 2008, pp. 1-4.
Parylene to silicon nitride bonding for post-integration of high pressure microfluidics to CMOS devices, *Lab Chip*, 2012, 12, 396, Ciftlik et al, pp. 396-400.
"Chamber and microfluidic probe for microperfusion of organotypic brain slices," *Lab Chip*, 2010,10, 326-334.
"Quantitative proteomic profiling of breast cancers using a multiplexed microfluidic platform for immunohistochemistry and immunocytochemistry," Kim et al, *J.biomaterials*, 2010, 10.040, pp. 1396-1403.
"Bioconjugated lanthanide luminescent helicates as multilabels for lab-on-a-chip detection of cancer biomarkers," Fernandez-Moreira et al, *Analyst*, 2010, 135, pp. 42-52.

* cited by examiner

FIG. 12 = Table 1 - Timing of the IHC assay applied on the microfluidic device for incubation time optimization studies. prAb and sdAb corresponds to primary and secondary antibody, respectively. For each biomarker, different incubation times are studied corresponding to $n = -2, -1, 0, 1, 2, 3, 4$

| Reagent | Flow duration (s) | Incubation time (min) | Step time (s) |
| --- | --- | --- | --- |
| Buffer | 7 | - | 7 |
| prAb | 5 | $2^n$ | $60(2^n)+5$ |
| Buffer | 7 | - | 7 |
| sdAb with fluorescent label +DAPI | 5 | $2^n$ | $60(2^n)+5$ |
| Buffer | 7 | - | - |
| Total per target | 31 | $2^{n+1}$ | $60(2^{n+1})+31$ |

FIG. 13 = Table 2 - Timing of a multiplexed IHC assay applied in a microfluidic device

| Reagent | Flow duration (s) | Incubation time (s) | Step time (s) |
| --- | --- | --- | --- |
| Buffer | 7 | - | 7 |
| $prAb_1 + prAb_2$ | 5 | 120 | 125 |
| Buffer | 7 | - | 7 |
| $sdAb_1 + sdAb_2$ with fluorescent label | 5 | 120 | 125 |
| Buffer | 7 | 7 | 7 |
| Total | 31 | 240 | 271 |
| Total per target without neg. cont. | 16 | 120 | 136 |

FIG. 14 = Table 3 – Provisional timing of IHC pre-processing of FFPE TSs applied in a microfluidic device

| Reagent | Flow duration (s) | Incubation or heating (s) | Step time (s) |
| --- | --- | --- | --- |
| Dewaxing (Xylene flow) | 30 | - | 7 |
| Rehydration (DI & Ethanol) | 60 | | 65 |
| Antigen retrieval solution and heating | 15 | 45 | 7 |
| Antigen retrieval | - | 120 | 65 |
| Buffer | 30 | - | - |
| Total | 135 | 165 | 300 |

FIG. 15 = Table 4 – Comparison of conventional IHC assay and previously demonstrated lab-on-a-chips with the present system

| System | Slide Type | Stained area per target | Reagent (μL) | Reagent Unit Cost | Minimum time per target (min) | Figure of merit Area/(vol*min*cost) |
|---|---|---|---|---|---|---|
| Conventional | Standard | 100% | 1000 | 2 | 120 | 4.15 |
| Our 1st generation | Standard | 38% | 33 | 10 | 20 | 52.34 |
| MMIHC | Standard | 1.5% | 30-60 | 0.1 | 90 to 154 | 55 |
| "The wave" | Standard | 100% | 250 to 350 | 2 | 15 | 132.5 |
| Our 2nd generation | Non-Standard | 100% | 180 | 10 | 3½ | 158 |
| This system non-mutiplexed | Standard | 100% | 200 | 1 | 2½ | 2000 |
| This system multiplexed | Standard | 100% | 100 | 1 | 1¼ | 8000 |

SAMPLE PROCESSING DEVICE WITH DETACHABLE SLIDE

This application is the U.S. national phase of International Application No. PCT/IB2013/051245 filed 15 Feb. 2013 which designated the U.S. and claims priority to CH 00256/12 filed 27 Feb. 2012, the entire contents of each of which are hereby incorporated by reference.

BACKGROUND OF THE INVENTION

In modern oncology, biomarker analysis is an indispensible tool for cancer diagnosis and prognosis. Immunohistochemistry (IHC) has been employed as a key tool for cancer biomarker analyses during routine pathology examinations for tissues in medical laboratories. IHC is an approved technique by many local and international authorities like Food and Drug Administration for biomarker analysis on tissue specimens and. In general, certain biomarkers, which are in fact antigens, are searched with specific primary antibodies with affinity to the target biomarker. Later, specific secondary antibodies that are conjugated with a label and have affinity to the primary antibodies are used for specific labelling. This label is commonly a fluorescent or coloured marker, and in case of fluorescence, the technique is called immunohistofluorescence (IHF).

On the other hand, IHC and IHF cannot be immediately applied to sample tissues but some pre-processing stages are needed. Pre-processing starts by a fixation step, where suspected histological samples that have been taken from patients first undergo a procedure that preserves the proteins and antigens inside the tissue, as well as the tissue's morphology. While many fixation techniques exist, commonly, the fixation step is done by either cryo-fixation, a very rapid cooling step involving use of liquid nitrogen, or formaldehyde fixation. Later, the tissues undergo the process of microtomy, where they are sliced into thin sections (4 μm-10 μm) and immobilized on standard glass slides. For subsequent and longer preservation, the cryo-fixated (CF) tissue sections are kept frozen while formaldehyde-fixed tissues are preserved by a layer of paraffin wax. The latter is called "formalin-fixed paraffin-embedded (FFPE)" tissue section. Following the fixation step, the cryo-fixated tissues can directly undergo an IHC procedure after being brought to ambient temperature, while the FFPE tissues need some further processing. These include the chemical elimination of paraffin and another step called antigen retrieval[1]. The antigen retrieval step helps recovery of the antigens that were cross-linked by formaldehyde using different means, including heating and enzymatic reactions.

[1] Antigen retrieval is also referred as "epitope retrieval" in many resources. In addition, if heating of samples are involved during antigen retrieval, it may also be referred as heat induced or heat mediated antigen retrieval.

Apart from manual processing in laboratories, the importance of the technique and need for routine diagnosis has triggered the development of commercial tissue processors for automation of the IHC process. These instruments are capable of processing a tissue section from antigen retrieval to staining and they are routinely employed in medical laboratories for diagnosis and prognosis. For the conventional instruments, the process time varies from 3 to 24 hours and they are generally capable of processing multiple slides.

Long Process Duration

Rather than advancement of the technique, it can be said that existing tissue processors only automatize and parallelize the manual process for enhancing the throughput and reproducibility up to a certain extent. One of the immediate problems is the long duration of the processing cycle. In general, the processes are run overnight and a processed and stained tissue can be obtained not earlier than the next day. This is currently a big obstacle of current IHC processes, since the needed time period does not allow analysis to be done during surgical interventions. However, if IHC could be done during the interventions, the surgical treatment protocols can be fine-tuned by using immediately the outcome from the IHC. One very important example is cancer diagnosis and its subsequent treatment steps. When a patient has been diagnosed with a cancer, the usual procedure is generally to realize a tissue biopsy for the suspected tissue. Then, these samples undergo an IHC analysis to see if the cancer suspicion is true. If the answer is yes, then a second surgery is conducted to clean all the tumour from the body, a critical step since even a single living cancer cell can grow up to a tumour again. Unfortunately, until now, there has not been a technique presented to verify that the tumour is completely clean. Hence, occasionally, patients may need additional surgery or chemotherapy to clean these cells that may have been left. When counted, the number of surgeries varies from 1 to 3, which increases risks, costs and anxiety for the patients, as well as a significant loss of health resources like doctors' time and surgery room availability.

The formal time for a procedure to be called intra-operative is less than 20 minutes. Until now, only one IHC system to reduce the time needed for IHC has been introduced. This technology is based on a phenomenon, called "the wave" mechanism and employs the 'wavy' hinged motion of two adjacent slides, one of which carries the tissue slice (PCT/US2006/015020 and WO/2006/116037). The technique can reduce the staining period of cryo-fixated slides down to 15 minutes and hence can be called intra-operative. On the other hand, these 15 minutes do not include fixation, observation and imaging time, where for a decision these may need at least around 15 minutes more, which exceeds the intra-operative condition. Therefore, the staining protocol duration should be reduced to less than 5 minutes in order to make the total IHC process 'intra-operative'. Moreover, although processing of cryo-fixated tissues is easier, FFPE tissues are more popular due to a number of reasons. First, in the cryo-fixation procedure, tissue preservation and archiving are more costly due to the needed equipment. More strikingly, cryo-fixated tissues show false negatives or false positives more frequently than the FFPE tissues. Therefore, FFPE is more convenient while cryo-fixation can provide faster results. The reported processing time for a FFPE tissue section using a "the wave" mechanism is 70 minutes, a time period close to that of conventional automated tissue processors.

Limited Accuracy in Quantitative Analysis

Apart from the intra-operative aspect, the accuracy of the obtained results with any technology until now is limited, when dealing with cases requiring quantitative biomarker expression analysis using the extent of the obtained signal by immunohistochemistry, as required during certain assays. Conventional techniques can produce ambiguous results up to 20% cases when such semi-quantitative analysis is required, and a final diagnostic result cannot be achieved using immunohistochemistry alone. Therefore, current standard is to subject these cases to a subsequent genetic analysis (in situ hybridization) in order to achieve a final diagnostic outcome, adding substantial cost and time (a few days) to the diagnostic process.

The inaccuracy of the quantitative immunohistochemical analysis has its origins in the intensity of an immunohistochemical signal, which is not necessarily proportional to the extent of antigen expression due to non-specific binding reactions, as well as unpredictable effects of tissue degeneration, variations in tissue fixation, paraffin embedding, and heat-induced epitope retrieval. Conventional IHC is a macroscale operation, in which reaction times in the range of 30 min to hours are required for achieving uniform exposure of surface antigens to bioreagents and reproducibility of outcome. This originates from long diffusion times, lack in precision of controlling and dosing of reagents, as well as limited fluidic exchange rates. In addition, long assay and antibody exposure times may result in significant adsorption and non-specific binding of the antibodies, so that the resultant immunohistochemical signal is no longer a linear function of the target biomarker concentration on the tissue. Scoring of these qualitative biomarker expression levels was often subjected to interpretation and experience of the pathologist.

However, if the proportionality between the biomarker expression levels and the immunohistochemical signal could be assured, the immunohistochemical signal will be quantitative and discrimination between positive and negative samples can be done with much higher accuracy.

In fact, this non-proportionality between the target antigens and the signal obtained from an immunoassay is not only specific to diagnostic immunohistochemistry or the immunohistochemistry in general. This problem exists in all settings where an immobilized target is present on the surface, and one or more detector reagent binds to this target at a rate limited by the diffusion speed of the detector reagents. These may include but not limited to immunocytochemistry, DNA hybridization, RNA quantification, aptamer and oligomer probes. Plus, the steric hindrance mechanisms can also contribute to this non-proportionality and compromises an eventual quantitative assay.

Requirement for Investing on Infrastructure, Equipment and Trained Personnel

State-of-the-art automated equipments have a few other drawbacks in addition to the intrinsic problems of long process duration and limited accuracy. Modern commercial automated IHC are bulky, supplied either in a bench or placed at the bench top. Therefore, they are far from being portable and hand-held. While being portable is not a requirement, for example for intra-operative operation, this may increase accessibility in remote places where a laboratory environment or electricity is missing.

In general clinics with a low budget and those that are located at remote places do not have the necessary infrastructure, equipment and expertise to be able to perform such kind of diagnosis. In fact, it is extremely expensive to form and maintain such a laboratory for a small sized clinic, requiring around 1M CHF investment on infrastructure and equipment, and more than 300K CHF per year for trained personnel. Therefore, required investment to form a laboratory that can perform immunohistochemistry is one of the major obstacles preventing accessibility of a large number of patients worldwide to this diagnostic technology One additional major obstacle caused by the current structure of a laboratory dictated by state-of-the-art equipment is the customization problem, which appears in particular when using for new biomarker discoveries and related research. The adaption of existing large scale diagnostic equipments to use with newly discovered molecules and biomarkers is both expensive and time consuming. This originates from the contradiction between the required flexibility in research & discovery and the extent of parallelization and throughput required by a central diagnostic laboratory. In addition, the central facilities resist such customization because either they are overloaded with the current diagnosis work or such customization may affect the later reproducibility. Hence, research tasks involving immunohistochemistry are in general done manually. However, when thought the large number of trials required to validate results and requirement for the reproducibility, the total time needed for manually completing such studies can span a few years, significantly affecting the total research and development costs of biomarker discovery.

The prior art can be summarized under 3 different sections constituting (a) Lab-on-a-chip devices performing IHC, (b) represented automated macro IHC processors reducing the process time and (c) Lab-on-a-chip devices made for other applications with similar microfluidic designs. Here, we summarize these and give a comparison in terms of a figure of merit.

Lab-on-a-Chip Devices Performing IHC

Until now, there had been a few microfluidic approaches to IHC for ameliorating certain aspects of the conventional IHC, which, can potentially benefit from decreased diffusion times and improved fluidic exchange control. Some of these are aimed to reduce total analysis time and others are aimed to perform multiplex IHC using multiple parallel small channels for searching different target biomarkers in spatially displaced locations with higher antibody dilutions. However, in none of these studies there had been an implication that a microfluidic approach results in an increase in accuracy of quantitative analysis and a decrease ambiguous diagnostic results obtained by such analyses.

Our group has represented a number of lab-on-a-chip devices engineered for IHC to reduce time-to-output. We have demonstrated a first-generation LOC in PDMS, which permits relatively fast analysis of tissues (20 min versus the conventional 2 h) [V. Fernandez-Moreira et. al. *Analyst*, no: 135, pp. 42-52, 2010]. Unfortunately, this device showed a limited analysis speed and detection area. The system was unable to hold high pressures, resulting in a maximum operational volumetric flow rate around 50 nL/s. The cumbersome assembly and disassembly of the system (manual integration) significantly increased analysis time and dead volume. Also, only part of the tissue slice could be exposed (less than a few 10% of the surface), thereby limiting the TS detection area.

Later, we demonstrated a second-generation device (A. T. Ciftlik et. al., *Proc. of 14th Int. Conf. on Miniaturized Systems for Chemistry and Life Sciences* (micro TAS '10), pp. 699-701, October 2010) again produced in PDMS, increasing the area and decreasing the incubation times down to 3.5 minutes. On the other hand, this device suffered from a number of problems that largely compromise the accuracy of quantitative analysis and its low-cost commercialization. The low accuracy originates from the eventual diffusion-controlled antigen-antibody reaction occurring inside the chamber, which also renders use of time-resolved fluorescence indispensable. The cross-section structure of the chamber and microfluidic channels connected to it form a structure as illustrated in FIG. 1. In the cross-section, the chamber is a wide and shallow rectangle, and the tissue section forms the bottom-wide side. The microfluidic channels are pipes about 50 µm high, and these channels are connected to the chamber on the shallow edges in the right and left-hand side, closer to the upper-wide side, which is found opposite to the tissue section. In such a design, when a fluid flow is induced by using the defined inlet and outlets on the shallow sides and closer to the upper-wide edges, the magnitude of fluid flow is significant only around the upper-surface, while it is much lower around to the tissue section. Hence, transport of IHC protocol reagents to the tissue surface still largely depends on slow cross-stream diffusion of the molecules from the upper surface. In addition, the design dictates that the chamber height should always be higher than the height of the microfluidic channels, and this condition renders the limiting role of diffusion in the transport of the antibodies even more significant. This prior design translates into a chamber that cannot be made lower than 250 μm, increasing diffusion times by a factor of 25, when compared to a 50 μm high chamber (see paragraph 0029). More strikingly, the slow diffusion-limited transport of the protocol reagents to the tissue surface compromises the proportionality between the obtained signal and the extent of antigen expression on the tissue surface, which makes a successful quantitative assessment of the immunohistochemical signal impossible.

Using short incubation times in such a diffusion-limited system (as described in paragraph 0016 and cited documents) was only possible when using advanced imaging equipment and materials. Due to such long diffusion times, only a small fraction of the primary and secondary antibodies can reach the tissue section surface when using short reagent incubation times in the protocol, and it was only possible to detect such low signals by time-resolved fluorescence. Time-resolved fluorescence is an advanced imaging technique, in which fluorophore excitation and recording of emission are done at non-overlapping time periods by making use of special time resolved marker-conjugated antibodies (lanthanides) which can continue emitting significantly long after excitation. Time multiplexing of excitation and emission processes largely eliminates the autofluorescent background signal originating from tissue and surrounding material, and makes very small amounts of bound (primary and secondary) antibodies on the tissue easily detectable. Using standard fluorescent imaging equipment and commercial fluorophores, it would not be possible to detect this signal. Nevertheless, both the fluorophores and microscopy equipment for time-resolved markers (lanthanides) are very expensive and non-standard, and conjugated diagnostic antibodies are commercially not available. As a consequence, the requirement for time-resolved microscopy constitutes another obstacle preventing successful and low-cost commercial implementation of this device, which, therefore cannot operate when employing standard staining reagents like fluorophores and chromogens.

Apart from the design-related problems that are listed above (paragraphs 0016-0017 and cited document), there are also a number of drawbacks due to the use of PDMS as a structural material. The relatively low Young's modulus of PDMS makes the channels susceptible to substantial deformation under higher fluidic pressures. That is, the flow characteristics might change under varying pressures and flow rates involved in a protocol. Moreover, in this prior design, the sealing of the integrated tissue section slide is done using PDMS that forms the walls of underlying inlet/outlet microchannels. Again, due to the low Young's modulus of PDMS, the force required for better sealing of the tissue slide can easily deform these channels, up to an extent that they are blocked and the operation of the device becomes impossible. These variations in the design dimensions and flow-rates due to easy deformation of the channels can introduce variations in the resultant IHC signal, and, when used for diagnosis, can largely compromise reproducibility of the results. In addition, the thermal properties of PDMS prevent the use of temperatures above 70° C., and PDMS is not chemically compatible with the many reagents, line Xylene, that may be involved in IHC protocols. Another drawback of this device is that it only accepts non-standard tissue section slide shapes, which constitutes a customization and hence a cost problem in commercialization issue of this structure as a diagnostic device.

To conclude, the described system in paragraphs 0016-0018 only improves the protocol time of the immunohistochemical assay, but this at the cost of using time-resolved fluorescence, which is an expensive and mostly inaccessible method in terms of required materials and infrastructure. Moreover, the assay time minimization does not eliminate diffusion-controlled transport of reagents to the tissue surface, and the ability to perform quantitative analysis that can be done with this system does not differ from a conventional setting: no quantification of tissue biomarkers is possible. Last but not least, the low Young's modulus of the system highly compromises the reproducibility due to possible deformations in the microfluidic structures that form the system.

Another approach presented in the literature is so called Multiplexed Microfluidic IHC (MMIHC) platform (M. S. Kim et. al, *Biomaterials*, Vol: 32, Iss: 5, pp. 1396-1403, 2011 and M. S. Kim et al. *PLoS ONE*, vol: 5(5): pp. e10441, 2010), having multiple small channels for searching different markers in spatially different locations. Having a response time of 90 minutes, the device is still in the time range of those of automated IHC processors. Moreover, the device can stain about 1.5% of the TS area, which is a drawback for generalization of the technique. Although authors have shown, for the specific case of breast cancer, that even for this small area there is about 85% correlation with a totally stained TS, a sufficient correlation cannot be achieved. It is also a cumbersome work to realize this correlation study for each different case. On the other hand, the authors have shown that they can decrease primary antibody concentrations by a factor 10, which is an important step to reduce expensive antibody consumption.

Commercial Automated Macro IHC Processors Reducing the Process Time

As it has been introduced before, the only processor in the market with low IHC process time is "the wave" system (PCT/US2006/015020 and WO/2006/116037). This technology is based on a phenomenon, called "the wave" mechanism and employs the 'wavy' hinged motion of two adjacent slides, one of which carries the tissue slice (Celerus Diagnostics). It can reduce the staining period of cryo-fixated slides down to 15 minutes and hence can be called intraoperative. On the other hand, these 15 minutes do not include fixation, observation and imaging time, where for a decision these may need at least around 15 minutes more, which exceeds the intra-operative condition.

Lab-on-a-Chip Devices Made for Other Applications with Similar Microfluidic Designs Vertical hole based devices accepting slides with immobilized specimens can be found in the literature. Mcneely et. al. (PCT/US2002/07113 and WO/2002/072264) introduced such a device made for DNA microarray processing. Rather than a wide-area chamber as needed in IHC, this DNA microarray processing device has multiple vertical holes and a network of microfluidic channels to deliver reagents to each small spot where an element of the DNA microarray exists. A similar device called "microfluidic probe" was also presented (A. Queval et. al. *Lab Chip*, vol: 10, pp. 326-334, 2010 and patent documents PCT/IB2010/052018 and WO/2010/128483), where vertical microfluidic holes arranged inside a very small spot (~100 μm in diagonal) to stain certain points in a tissue or cell monolayer, where this probe head can be moved spatially. In another patent by Delamarche et. al. (PCT/IB2003/005350 and WO/2004/050246), a device for flowing a liquid on a surface has been introduced, where vertical holes and a spacer is used to form a chamber on the surface.

Additional DNA hybridization (US/2006/0003440) and sequencing devices (PCT/US2010/047392 and WO 2011/026136) made with similar techniques are also present, where they also consist of vertical holes connecting to microfluidic channels with immobilized DNA. Adey (PCT/US02/24616 and WO/2003/015922) has described another device having a low volume chamber for DNA and RNA processing with a flexible deflecting membrane to change the chamber height depending on the application. Kim et. al. (PCT/US2008/074865 and WO/2009/029845) also describe a device for a wide-area microfluidics, having a semicircular inlet hole and a triangularly shaped outlet hole uniform distribution.

Among the studies with vertical microfluidic holes, a wide-area and uniformly reagent distributing device operating in very short times with high-pressure resistivity has not been represented. In none of the above devices and studies, there had been an implication that a microfluidic approach results in an increase in accuracy of quantitative analysis of immobilized targets and a decrease ambiguous results obtained by such analyses. In addition, the lab-on-a-chip IHC processors either semi-manual as in the case of MMIHC where only primary antibody incubation is done on-chip, can stain only a proportion of the TS or has high reagent costs.

Brief description of the drawings and tables

FIG. 1—Cross-section structure of the chamber and microfluidic channels connected to it form a structure as illustrated.

Figure 2A:
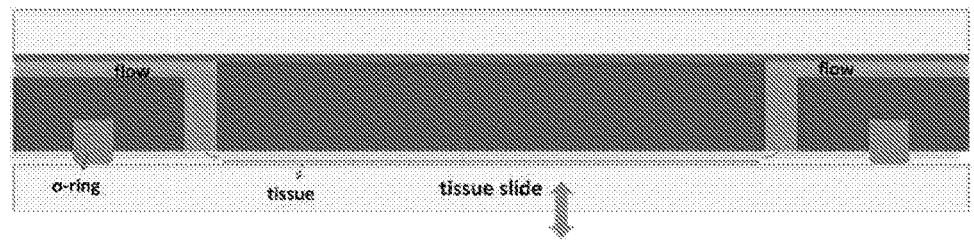

FIG. 2A—Cross-section representation of the device having microfluidic access holes located along the edges of the tissue chamber for in- and out-flow.

Figure 2B:
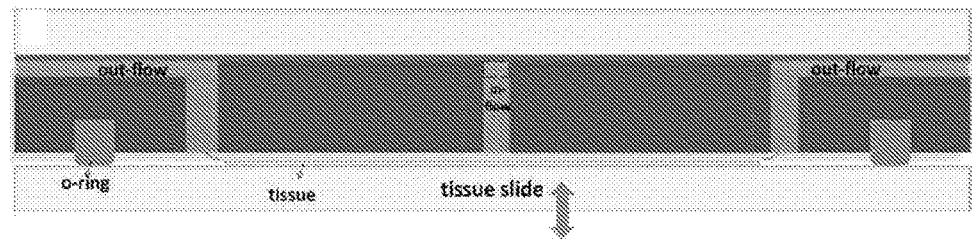

FIG. 2B—Cross-section representation of the device having microfluidic access holes located at the center of the chamber for the in-flow and at the edges of the chamber for the out-flow.

Figure 3:
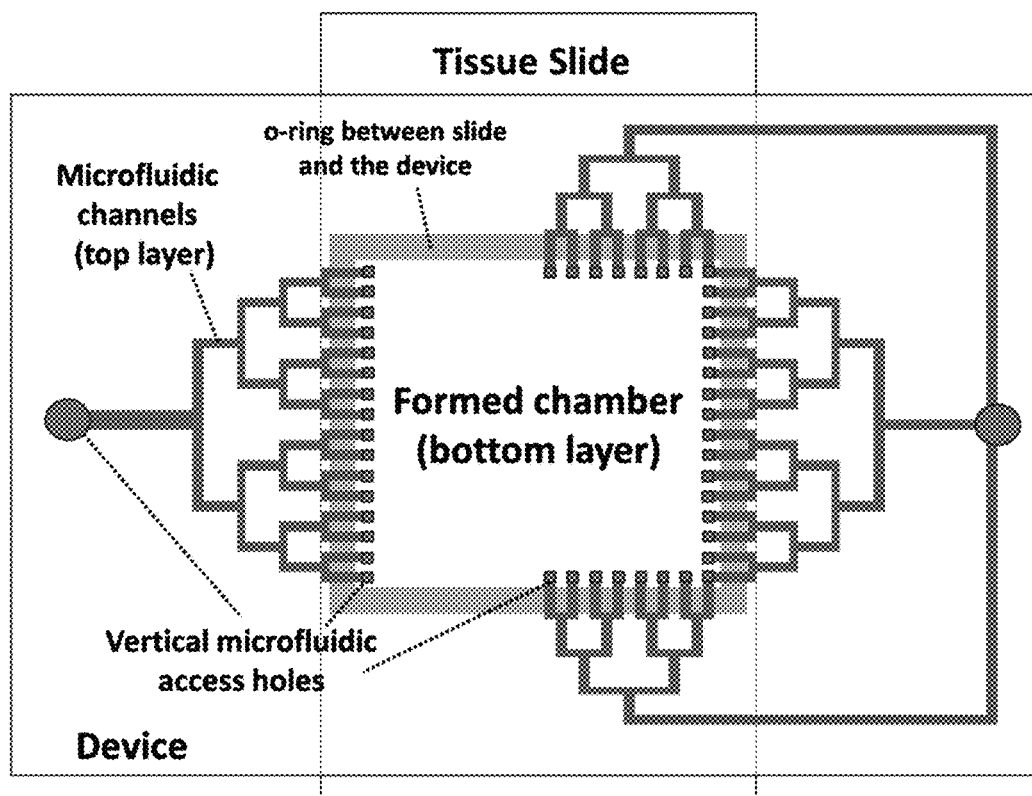

FIG. 3—Top view of the distributed network channel made in the top layer and also the microfluidic access hole arrangement.

Figure 4:
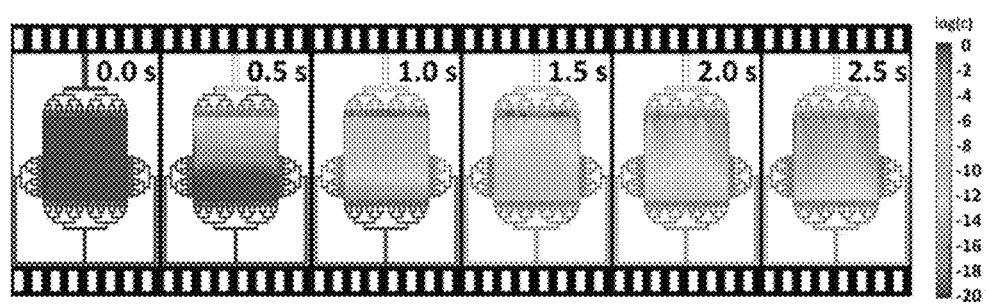

FIG. 4—Finite Element Method (FEM) simulations of the convection in the tissue chamber with distributed network channels for a 10 pL/s flow rate for a 50 pm chamber height.

Figure 5:
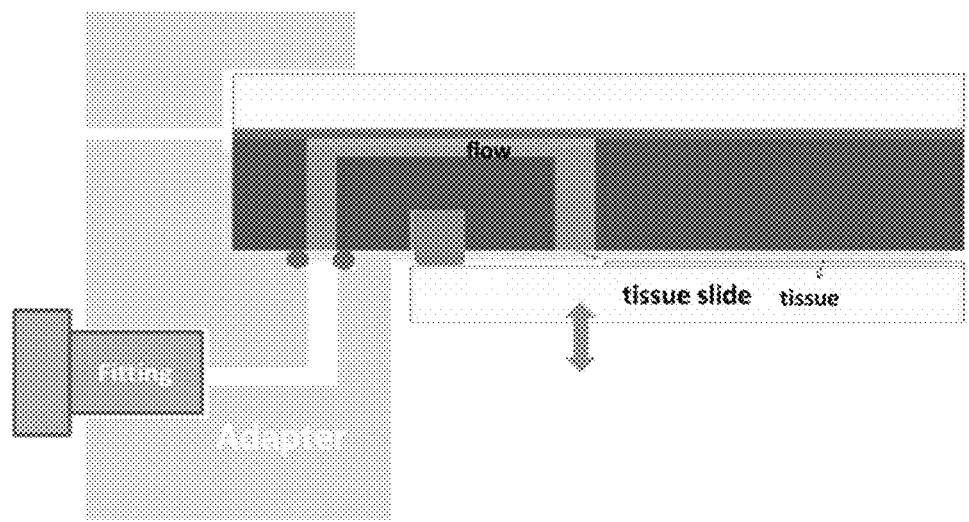

FIG. 5—Integrated device cross-section, where the system is composed of a macro-machined adapter for easy integration and the micromachined chip for microfluidics and tissue staining.

Figure 6:
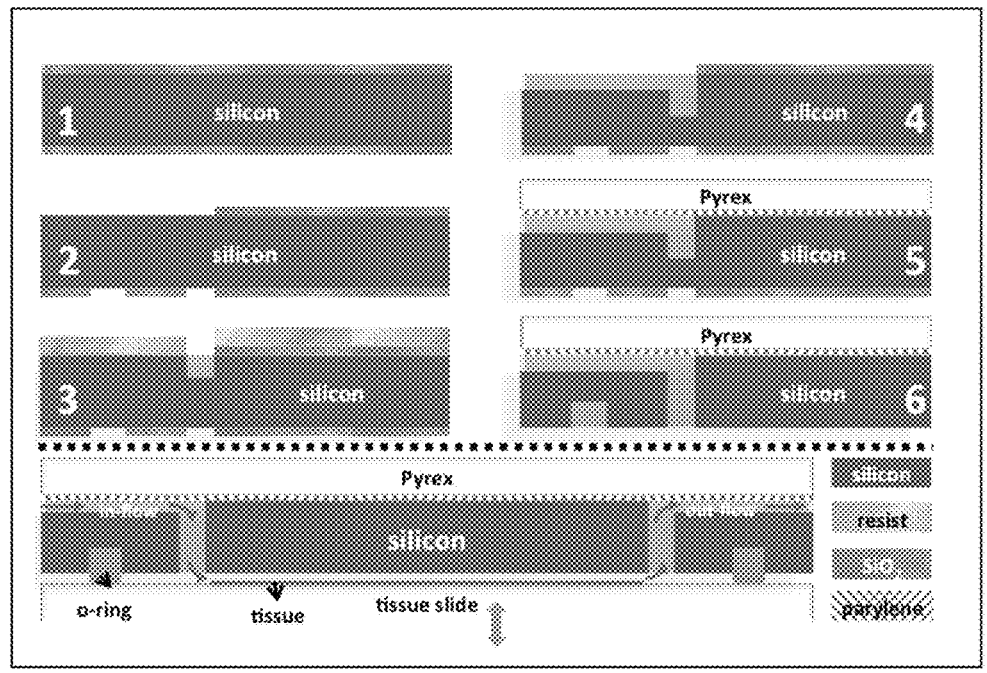

FIG. 6—The microfluidic devices are made by multi-step deep reactive ion etching (DRIE) of microfluidic trenches and subsequent bonding with a Pyrex wafer coated with Parylene-C as illustrated, for achieving higher precision and burst-pressures.

Figure 7A:
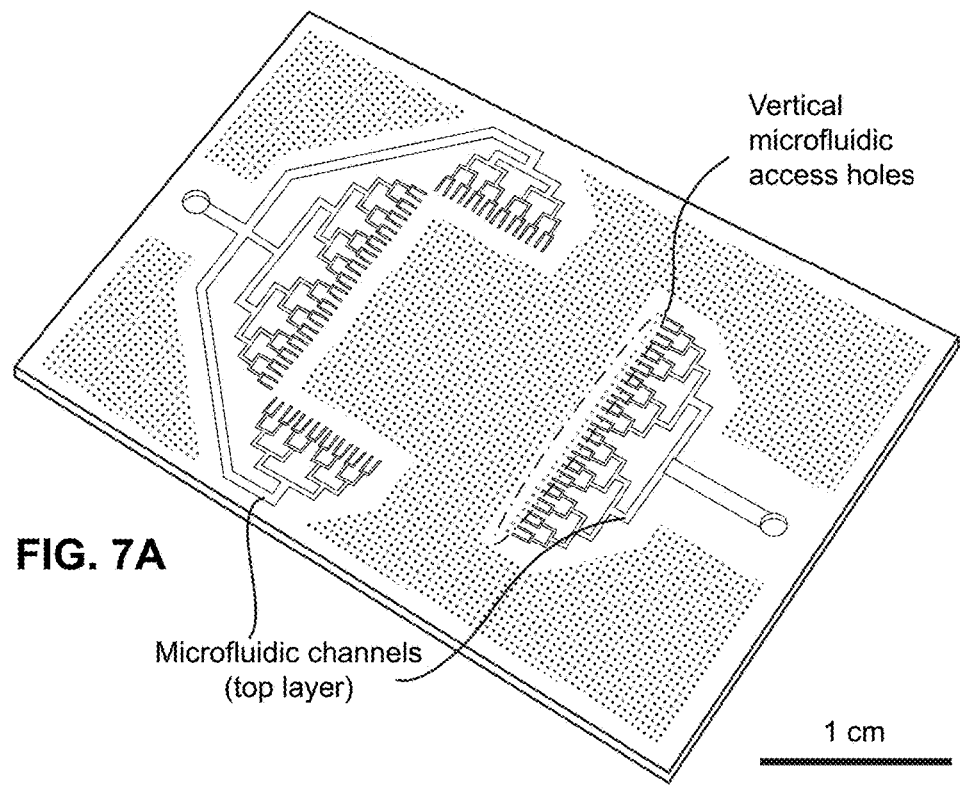

FIG. 7A—Shows the microfluidic channels in the top layer of the device after fabrication and dicing.

Figure 7B:
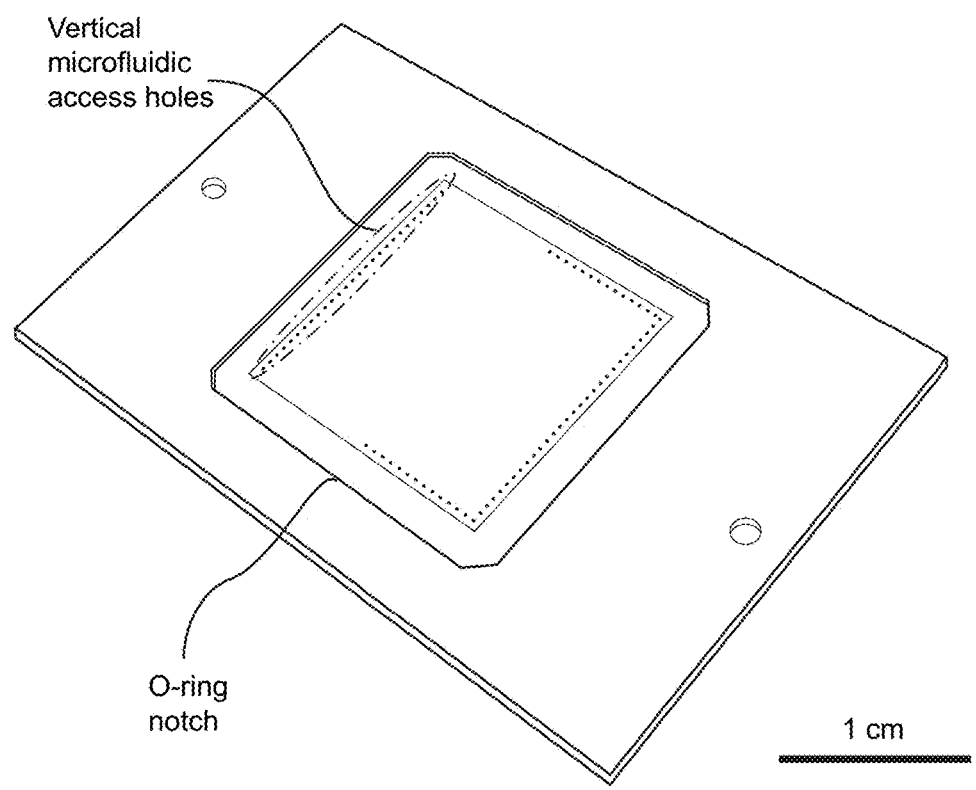

FIG. 7B—Shows the microfluidic access holes together with the notch where the o-ring is placed, located at the bottom side of the device.

Figure 7C:
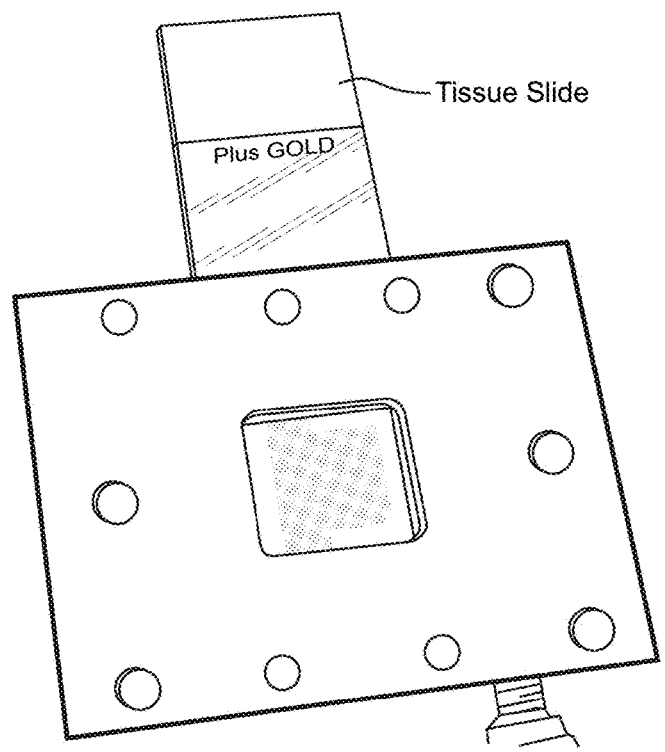

FIG. 7C—Shows incorporation of a standard TS into the integrated system.

Figure 7D:
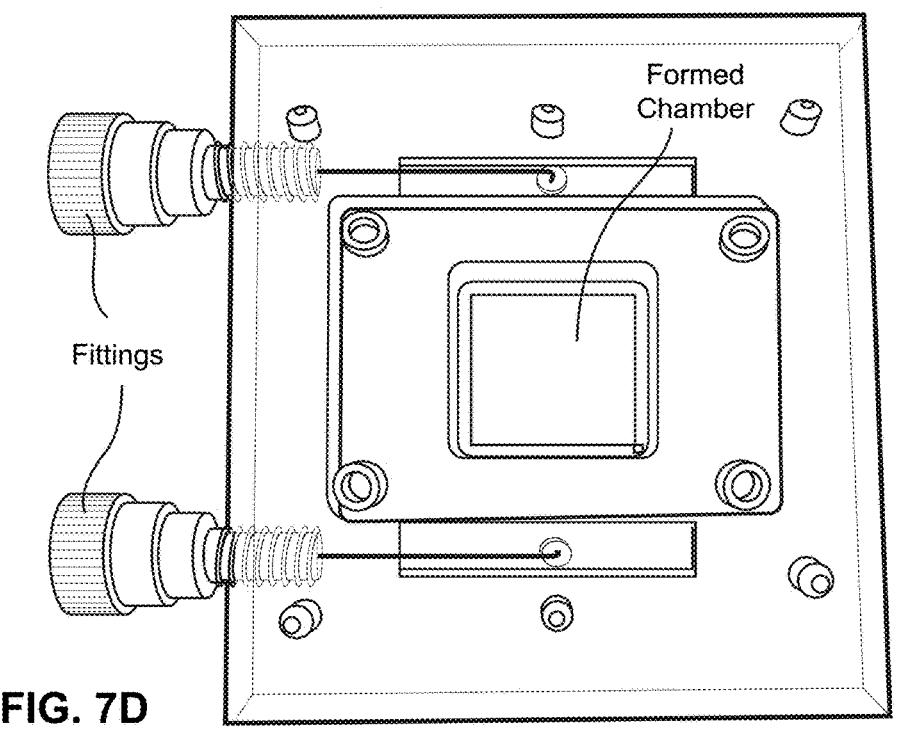
Figure 8A:
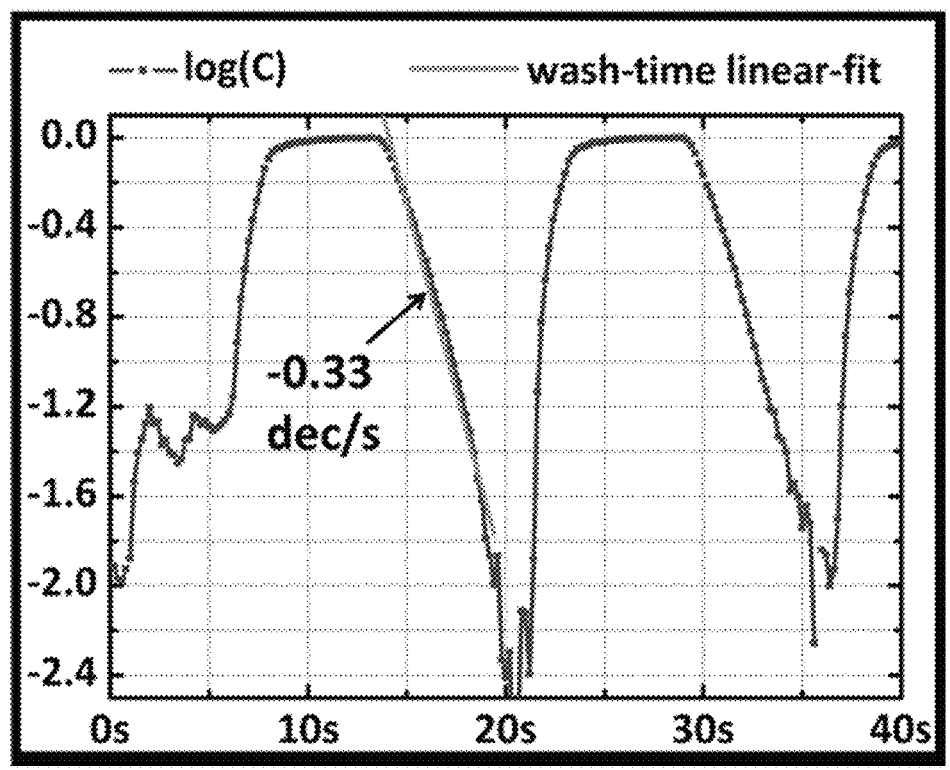
Figure 8B:
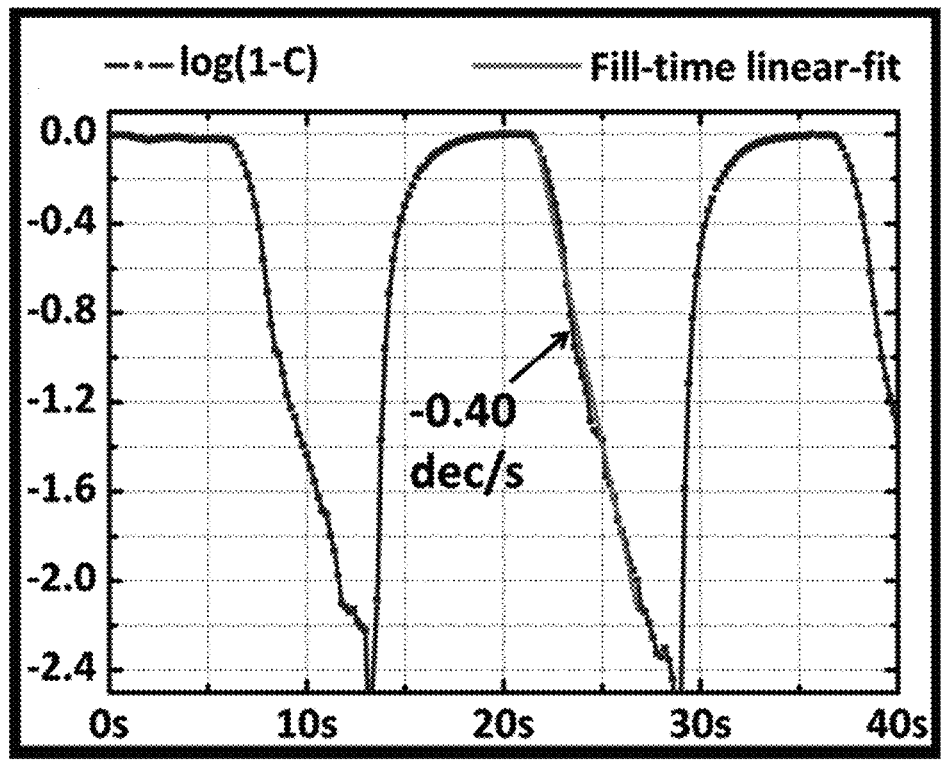
Figure 8C:
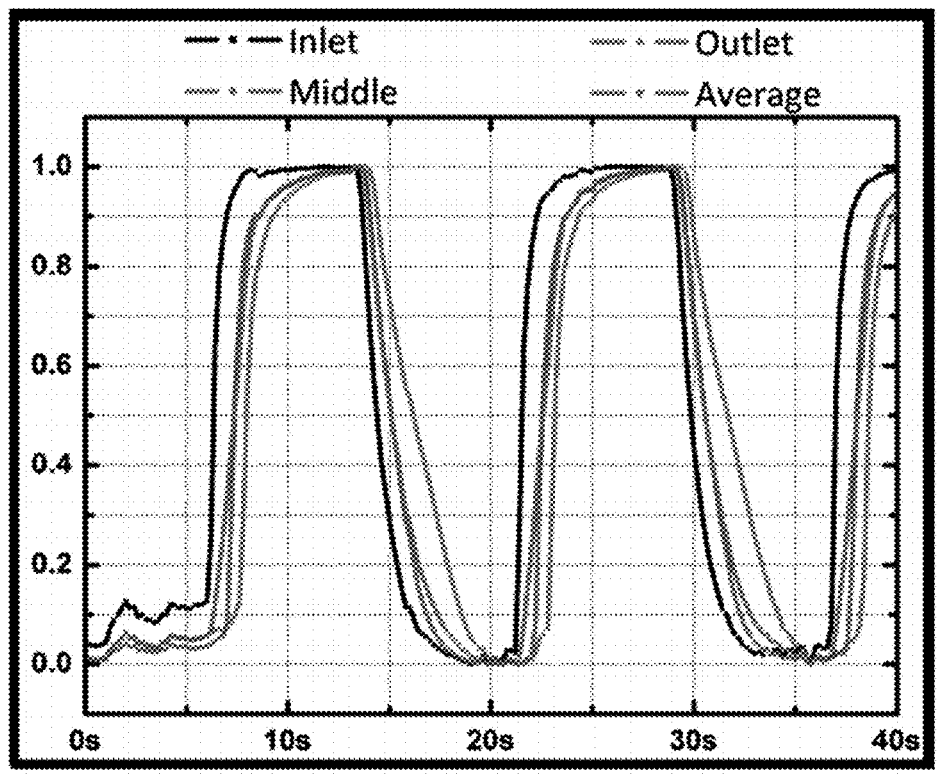
Figure 8D:
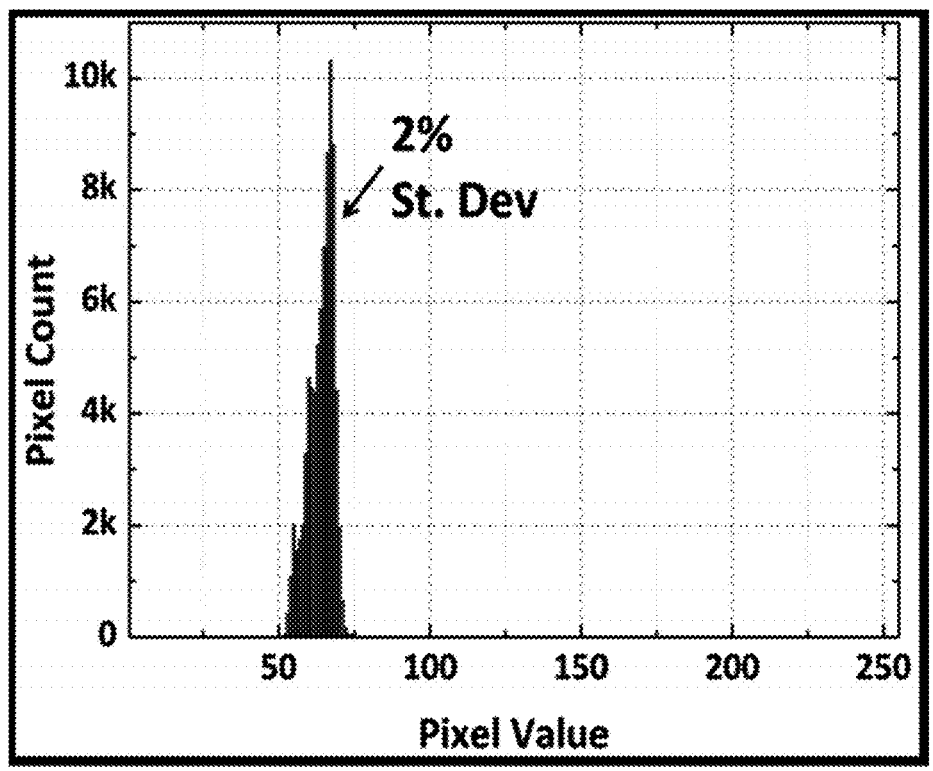
Figure 9A:
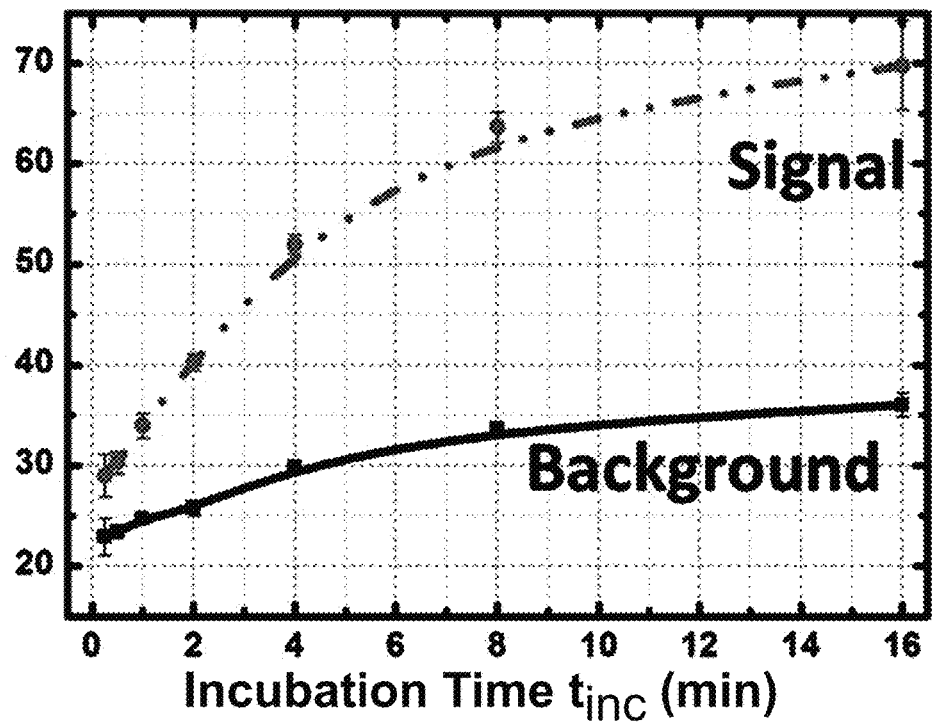
Figure 9B:
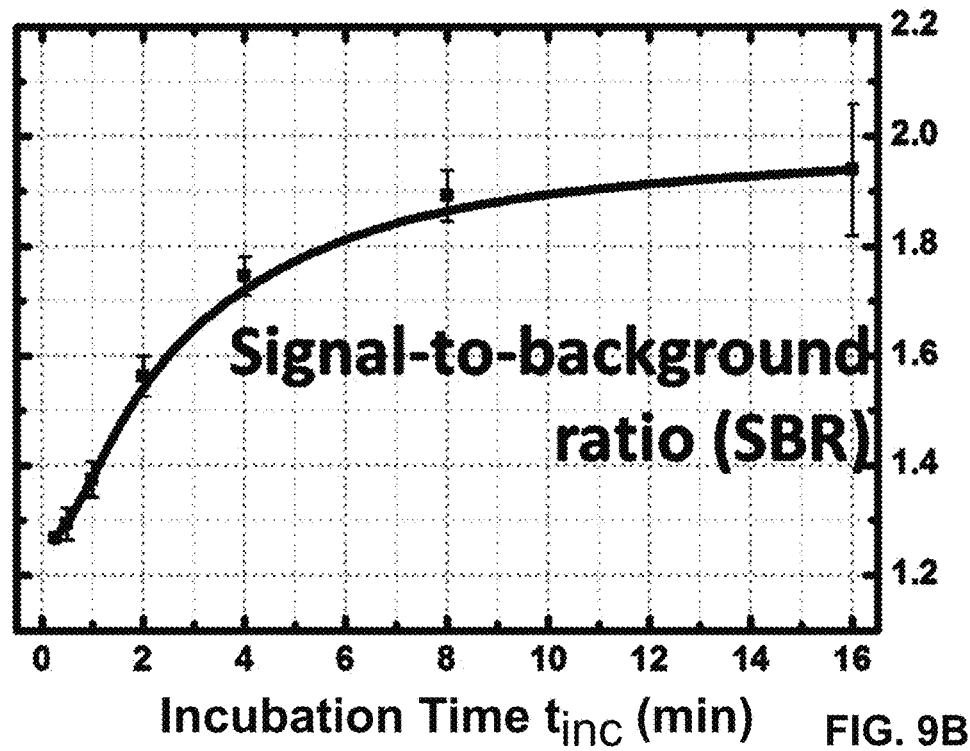
Figure 9C:
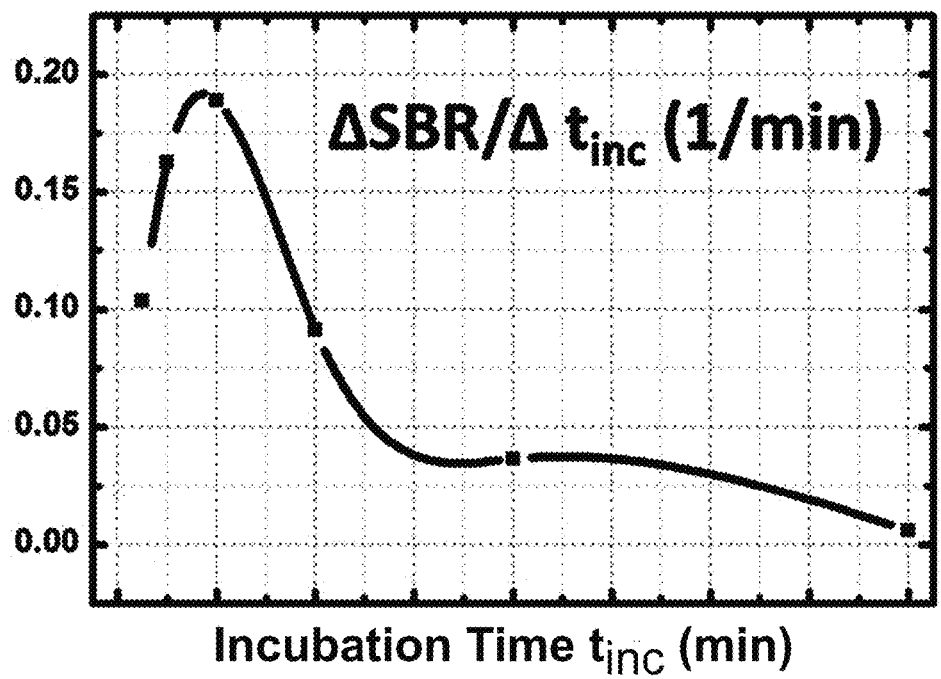
Figure 9D:
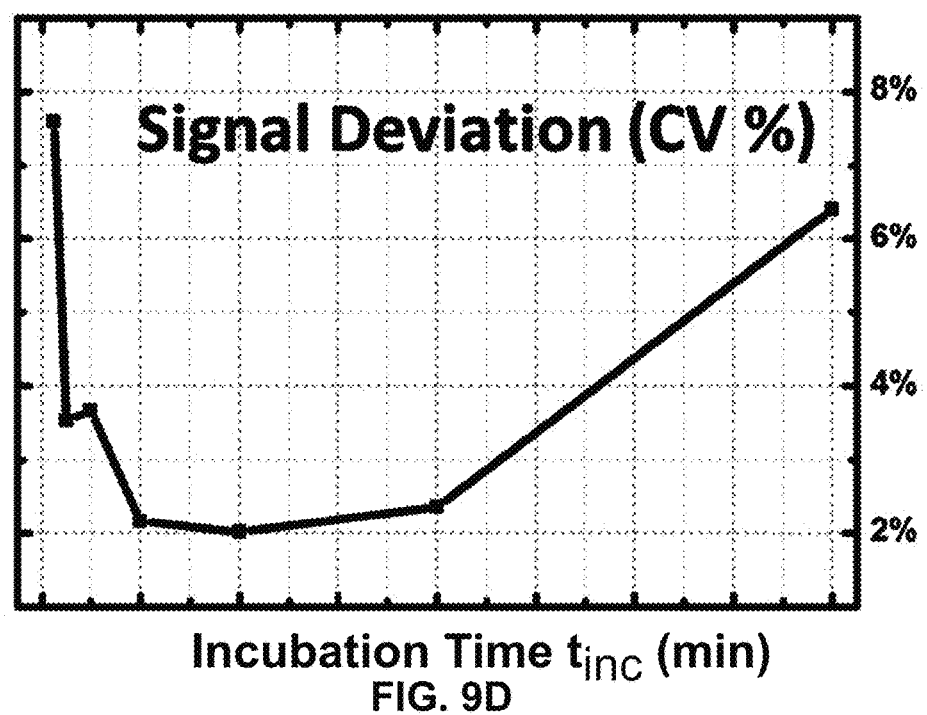
Figure 10A:
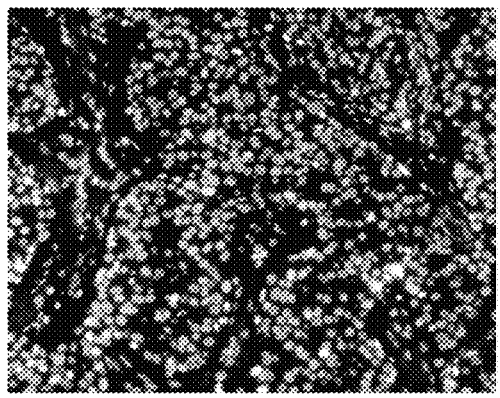
Figure 10B:
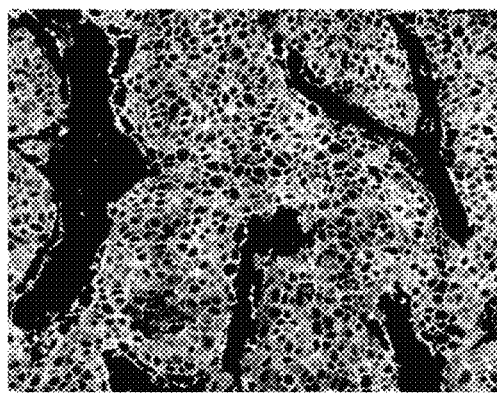
Figure 10C:
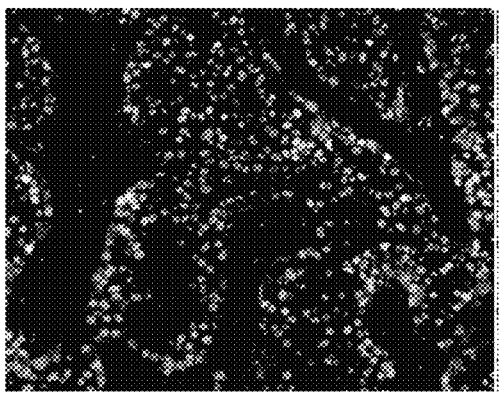
Figure 10D:
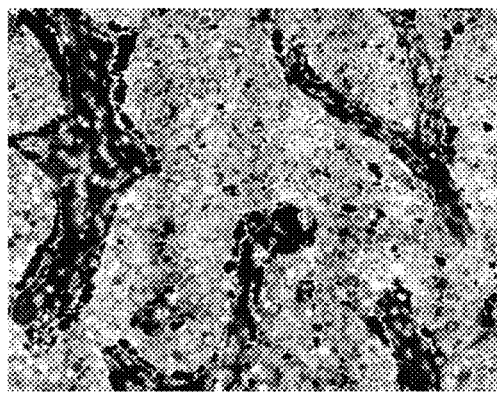

FIG. 7D—Shows the integrated system with the formed tissue chamber.

FIGS. 8A, 8B, 8C, 8D—Show plots of response time and uniformity measurements.

FIGS. 9A, 9B, 9C, 9D—Show optimization of protocol time.

FIGS. 10A, 10B, 10C, 10D—Show example multiplex fluorescent detection of breast cancer biomarkers human epidermal growth factor receptor (HER2/neu)and Estrogen Receptor (ER) using immunohistochemistry with the system.

Figure 11:
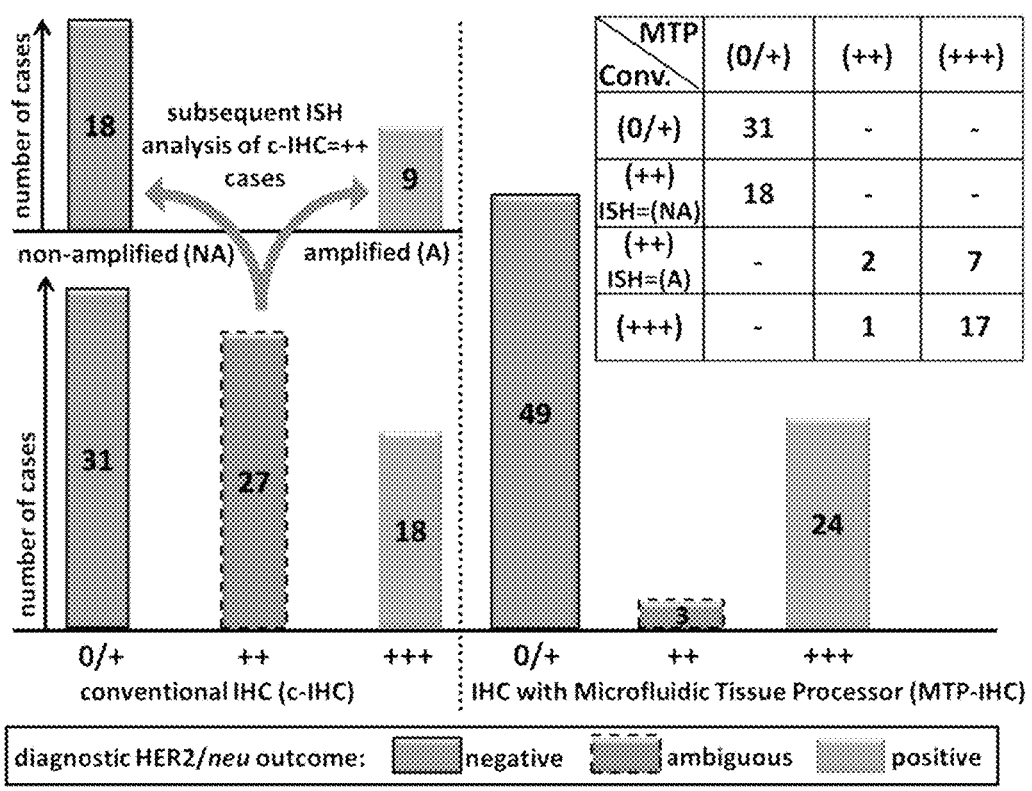

FIG. 11 shows the comparison of diagnostic outcomes between conventional IHC and MTP-IHC.

FIG. 12=Table 1—Timing of the IHC assay applied on the microfluidic device for incubation time optimization studies.

FIG. 13=Table 2—Timing of a multiplexed IHC assay applied in a microfluidic device.

FIG. 14=Table 3—Provisional timing of IHC pre-processing of FFPE TSs applied in a microfluidic device.

FIG. 15=Table 4—Comparison of conventional IHC assay and previously demonstrated lab-on-a-chips with the present system.

DESCRIPTION OF THE INVENTION

The invention relates to a device and a process as defined in the claims.

It refers in particular to a Microfluidic Tissue Processor (MTP) for accurate biomarker detection in clinical immunohistochemistry. A large area (256 mm$^2$) and shallow (<100 µm) chamber is formed by clamping a standard microscope slide carrying a breast cancer tissue slice with a glass/silicon micro-machined structure, which incorporates access holes for rapid and uniform exposure of the tissue slice to the immunoassay bioreagents. The microfluidic flow patterns combined with the small vertical diffusion length in the shallow chamber allow to use bioreagent incubation times as short as 2 min. This allowed accurate quantitative analysis by preserving the proportionality between the surface target amount and the resultant signal.

Microfluidic Device Design

Fast assembly of the tissue slides (TS), which are simply standard microscope slides with immobilized tissue sections, to the microfluidic channels is quite important since the overall assay time is a critical parameter. In addition to fast assembly, we conceive a system, in which we need to change only the TS, while other aspects (the microfluidic circuit) are kept unchanged FIG. 2 shows the cross-section representation of the device having microfluidic access holes located (a) along the edges of the tissue chamber for in- and out-flow, and (b) at the center of the chamber for the in-flow and at the edges of the chamber for the out-flow. The device has lateral microfluidic channels for guiding and pre-conditioning of the fluid for delivery to the TS, using a top microfluidic layer and vertical microfluidic access holes for accessing the thin chamber, which is formed by sealing the TS to the microfluidic channel device part using an o-ring.

Unlike the previously represented systems where the chamber is directly accessed from sides (see paragraphs 0016-0019), these microfluidic channels are connected to the tissue chamber by vertical microfluidic access holes. This arrangement permits adjustment of the top-layer microfluidic channel parameters (thickness, structure, pressure-holding capabilities etc.), independent of formation and structure of the tissue chamber. Since the pressure-holding capability of the tissue chamber is also determinant for the assay time, the sealing of the microfluidic chamber with the TS is very critical. Here, the sealing was made by a customized o-ring using polydimethylsiloxane (PDMS)

molding. With this design, the applied sealing force only affects the chamber thickness and pressure holding capability of the chamber itself, and this sealing mechanism is mechanically decoupled from the rest of the microfluidic system.

In addition, this design allows the chamber height be much lower than previous systems (see paragraphs 0016-0019). In particular, the tissue chamber height is only determined by the selection of the o-ring thickness with respect to the o-ring notch and also the applied sealing force to the TS. In fact, the thickness of the chamber is a critical parameter, since it directly affects the incubation time of reagents used in the IHC process, which is dictated by slow diffusion of the relatively large antibody molecules. When the device is integrated with the TS, a tissue chamber is formed having a thickness between 50 µm and 100 µm. For commonly used antibodies like mouse anti-human IgG molecules, we have calculated that an incubation time of 1 minute requires a chamber height less than 100 µm. On the other hand, reducing the chamber height below 50 µm is possible, but may potentially result in detachment of tissue from the TS during high-pressured fill-and-wash cycles and increase total flow durations.

The ability to form such shallow fluidic chambers is key for shifting the main transport mechanism from diffusion to advection. Modifying the dominant transport mechanism of the reagents in the chamber is key to prevent diffusion-controlled reactions, which compromise proportional staining of immobilized targets and render quantitative analyses inaccurate. Not only a minimal chamber height, but also the microfluidic access hole design contributes to accurate quantification, by directing the fluid flow to the surface of the integrated TS as shown in FIG. 2. Such direction of the fluid flow enables advection-mediated transport of the reagents to the tissue surface, and allows the immunohistochemical reactions to happen in the reaction-controlled regime.

In order to increase the available staining area of the device to 100%, a large chamber with dimensions 16 mm by 16 mm has to be realized. A uniform fluid distribution inside such chamber is critical for delivering equal amount of reagent and washing solutions per unit time to each part of the tissue. Hence, we adopted a distributed microfluidic channel network structure, which equalizes flow throughout the chamber. FIG. 3 shows a top view of the distributed network channel made in the top layer and also the microfluidic access hole arrangement. The arrangement of the microfluidic access holes aims realizing an uniform distribution of reagents inside the chamber. On the other hand, the distributed microfluidic channel network structure ensures equal delivery of reagents throughout the tissue chamber. In principle, one can increase the chamber area to 25 mm by 50 mm by resizing the chamber, microfluidic channels and hole arrangement accordingly.

FIG. 4 shows Finite Element Method (FEM) simulations of the convection in the tissue chamber with distributed network channels for a 10 µL/s flow rate for a 50 µm chamber height (COMSOL® Multiphysics). This simulation suggests that after 2.5 s of buffer wash, the achieved concentration of the previous reagent is only $10^{-12}$ of its initial concentration in the worst case. Hence, we expect no dead-surface locations that would need order-of-magnitude higher wash and fill times. The distributed network channel work effectively, as given by FEM simulations in FIG. 4, only if it is combined with a tissue chamber that is thin enough to be considered as two-dimensional. While previous works showed similar microfluidic channel network structures (see paragraphs 0016-0019 and FIG. 1), their cross-section structure prevented the reagent supply directly to the TS surface by advection. That is, the reagents were delivered to the top side of the chamber opposite to the location of the tissue surface, and the transport of the reagents to the tissue surface was completely dominated by diffusion. In contrast, the present device, which has a mechanically decoupled tissue chamber and microfluidic channel network connected to the chamber via microfluidic access holes, demonstrates all advantages of the simulated advective transport (see paragraph 0037-0038 and FIG. 8).

The integrated device cross-section is shown in FIG. 5, where the system is composed of a macro-machined adapter for easy integration and the micromachined chip for microfluidics and tissue staining. The microfluidic device is permanently integrated with the adapter part, while only the TSs are assembled and disassembled between analyses. This configuration is needed for accessing the microfluidic device with standard commercial fluidic adapters. Moreover, such integration of the external tubing permits utilization of fluid pressures of more than 200 bar.

A system that can perform sequential treatment without cross-contamination between reagents is quite important to realize biomedical staining protocols reliably. In our case, IHC assays with 3 reagents are needed for each target. For this purpose, a microfluidic inlet lane has been made in the adapter structure, which can combine commercially available single direction check valves. These check valves, are vital in preventing cross-contamination as well as in blocking the external fluidic system during assembly and disassembly of the TS. During operation, pressure is applied to the syringe of the required reagent, which opens the corresponding check valve and releases fluid inside the tissue chamber, while the other syringes are kept unpressurized, hence sealed from the tissue chamber. Such integration also improves throughput, since we prevent refilling the large dead-volume of the external microfluidic system in each replacement. On the other hand, if integration of miniaturized check-valves into the device is made, the dead-volumes and flow times can be reduced more.

Microfabrication

In the present invention, the microfluidic devices are made by multi-step deep reactive ion etching (DRIE) of microfluidic trenches and subsequent bonding with a Pyrex wafer coated with Parylene-C as illustrated by FIG. 6, for achieving higher precision and burst-pressures. 1) A 4 inch silicon wafer with 2.5 µm of wet oxide has been taken as a start. 2) Then 5 µm AZ9260 photoresist was spun, exposed with the DNC mask and developed to form the channels. The oxide underneath was etched with RIE (Alcatel 601E). 3) The resist is stripped and an additional lithography step was realized using a 5 µm AZ9260 photoresist (MicroChemicals GmbH, Germany) and chamber mask. After the lithography, the front side is DRIE etched (Alcatel 601E) in two steps. This was to form channels and chambers at different heights. First, the chamber was etched 100 µm deep and the resist was stripped. 4) After the resist strip, the channels were etched via the patterned hard mask in the first step. The etch depth has been varied between 50 and 200 µm depending on the design. 5) Later, this wafer is bonded to a 2 µm Parylene-coated Pyrex wafer by a low stress Parylene-C bonding procedure. Note that, anodic bonding can also be used in this step, but this may induce higher stress and cracks. 6) After bonding, an additional lithography step was applied to the bonded stack from the silicon side with a 8 µm thick AZ9260 resist. Later, one more step of DRIE is performed until the chamber is reached, which was also used to generate notches for o-ring attachment. Finally, the resist is stripped. Fabrication is finalized by dicing the wafer. FIG. 7 (a) shows the microfluidic channels in the top layer of the device after fabrication and dicing. FIG. 7 (b) shows the microfluidic access holes together with the notch where the o-ring is placed, located at the bottom side of the device.

Used materials and the microfabrication technique in the present invention eliminate previous drawbacks due to the use of PDMS. Si and $SiO_2$ have much higher Young's modulus than PDMS, which makes the microfluidic channels resistant to deformation under higher fluidic pressures, and allow applying fluidic pressures up to 16 MPa (A. T. Ciftlik et. al. Lab Chip, vol: 12 pp. 396-400). When compared, PDMS-made systems are limited to pressures of around 0.7 MPa (M. A. Eddings et. al. J. Micromech. Microeng., 18, pp. 067001). Therefore, in our design, the flow characteristics will be stable, even under much higher pressures and flow rates, which might be involved in an IHC protocol. In addition, thanks to the high rigidity of the used materials and the mechanical decoupling explained above (see paragraph 0028), the force required for better sealing of the tissue slide does not impose any constraints, and the microfluidic channels stay intact. Therefore, the variations in the design dimensions and flow-rates due to deformation of the channels remain negligible. Hence, a precise protocol application is possible, and when used for diagnosis, this precision ensures reproducibility. In addition, the present device can work up to 200° C. and is much more robust in terms of chemical compatibility with the reagents that may be involved in IHC protocols. Moreover, it accepts standard tissue section slide shapes, which does not require any customization, and the commercialization of this structure as a diagnostic device is straightforward with the standards used in the clinical practice. FIG. 7 (c) shows incorporation of a standard TS into the integrated system, and FIG. 7 (d) shows the integrated system with the formed tissue chamber.

Device Performance and Clinical Results
Concentration Response Time and Uniformity Characterization The concentration was characterized by analyzing the intensity profiles of the tissue chamber from the obtained images using open-source ImageJ software. For the analysis, videos with 5 frames per second are converted to gray-scale. First, the maximum concentration intensity (MxCI) was experimentally found by calculating the average intensity throughout the chamber for a long time (100 s min) with a flow rate of 40 μL/s. Similarly, the minimum concentration intensity (MnCI) was experimentally found after flowing PBS buffer solution. These two values are used to normalize the intensity recorded in the experiments and normalized values are used as reagent concentration, C, which ranges from 0 to 1. Later, we applied the reagent and buffer solutions both applied in the form of a square waveform with a 16 s period and 50% duty cycle, but with a 180° phase shift. From the resulting videos, the response time of concentration changes in different regions of the tissue chamber were studied, as well as the averaged behavior. The generated response time curves are used to evaluate the possible time performance of our device. Therefore, we used straight line fitting in logarithmic plots of C and 1-C. These fits give fill and wash performance in terms of decades per second (dec/s), an indicator for calculating required wash and fill times for given fill/wash purity. On the other hand, concentration uniformity throughout the tissue chamber was calculated by dividing the standard deviation of pixel histogram of tissue staining area to camera pixel depth at the instant of complete fill and wash.

The plots of the response time and uniformity measurements are given in FIG. 8. FIG. 8 (c) shows the concentration response of different tissue chamber regions located around inlet, middle and outlet of the chamber, as indicated. While there is an obvious lag in concentration response between inlet and outlet, the total time of reagent application is the same. This is quite critical for reproducibility of results, since extended or short exposure of certain regions of tissue to antibodies and staining may result in false target expression levels. We have also observed that the average intensity throughout the chamber is very close to measurements in the middle of the chamber. Hence, for situations where a high optical magnification of a particular part of the tissue slice is needed, one can use the middle of the chamber since the rest of it cannot be monitored anyway. The logarithmic plots of C and 1-C, calculated by averaging whole tissue chamber, are given in FIGS. 8 (a) and (b), where the mean of best line fit slopes are shown for wash and fill cycles. A fill performance of −0.40 dec/s is observed, which means 5 s of fill is needed to achieve 99% of the reagent concentration at the inside of the syringe. Similarly, the wash performance was −0.32 dec/s, indicating that 7 s of buffer was enough to decrease the concentration beneath 1% of initial value. We think that the discrepancy between two is due to the diffusion of molecules, which favors the fill cycle but compromises the wash. FIG. 8 (d) shows the pixel histogram of the chamber in filled states, which demonstrates 2% concentration non-uniformity throughout the chamber after 5 s of filling.

Optimization of Incubation Time for Proportional Detection of Biomarkers on a Cancerous Tissue Having demonstrated the time response of the microfluidic chamber, we turned to the analysis of diagnostic biomarkers on human breast cancer tissues. Based on the previous analysis, a sequential protocol needs to be developed, as well as an optimum incubation time that generates fluorescent images with a reproducibly high signal-to-background (SBR) ratio in positive cases. In this optimization study, we used 7 HER2/neu-positive tissue slices with strong expression, which were cut adjacently from the same tumorectomy sample, for different incubation times ($t_{inc}$) of the primary and secondary antibodies to establish the incubation conditions and the incubation time has been varied logarithmically, taking $2^n$ minutes of incubation with n=−2, −1, 0, 1, 2, 3, 4 to evaluate the effect of incubation time on resultant signal from 15 seconds to 16 minutes. This is in conjunction with the device design suggesting a 1 min diffusion duration from center to tissue slice surface after fill and the above set of incubation times constitutes logarithmically distributed cases around the theoretical value.

FIG. 9 shows the optimization of protocol time. (a) Fluorescence intensity obtained for HER2/neu-positive tissue slices, which were cut adjacently from the same tumorectomy sample, for different incubation times ($t_{inc}$) of the primary and secondary antibodies. (b) Signal-to-background ratio (SBR) with respect to incubation time, obtained by taking the ratio of signal and background values of (a). The major part of the SBR develops linearly during the first 2 minutes of the incubation, suggesting that immunoreactions are in the kinetic regime on this timescale. (c) Rate of change of SBR per additional incubation time. The rate is maximum at $t_{inc}$=2 min and start decreasing when the tissue slices were subjected to longer incubation times. (d) Study of the coefficient of variation (CV) in the signal value level calculated for different regions on the same tissue slice expressing the target antigen. A reproducible signal uniformity with a coefficient of variation (CV) around 2% is observed for incubation times ($t_{inc}$) between 2 and 8 min.

After the tissue preparation and antigen retrieval, protocols shown in Table 1 are applied to tissue slices, where reagent fill and buffer wash times were chosen as 5 s and 7 s, respectively. Following the protocol applied on MTP, the microscope slides are taken out, coverslipped and image acquisition has been done with a scanning fluorescent microscope. Later, these images are used to obtain the signal values by taking the average of the fluorescence intensity over the image pixels that correspond to HER2/neu-expressing regions located in the cell membrane of cancer cells. Similarly, the background values are obtained by averaging the fluorescence intensity over the rest of the pixels (FIG. 9 (a)). The plot of SBR calculated for each incubation time as shown in FIG. 9 (c), where it can be seen that even for the protocol with n=−2, the signal is detectable and the SBR only improves from 1.2 to 1.90, when we increase the incubation time 64 times for the HER2/neu case. The major part of the SBR develops linearly during the first 2 minutes of the incubation, suggesting that immunoreactions are in the kinetic (reaction controlled) regime on this timescale, and later being controlled by diffusion. We have also studied the coefficient of variation (CV) in the signal value level calculated for different regions on the same tissue slice expressing the target antigen. A reproducible signal uniformity is observed and, although decreasing with time, CV stabilizes after n=1 (FIG. 9 (d)).

We have chosen the protocol with n=1 (2 min of incubation time) as eventual protocol for using in our clinical study. The major reason is that for n≤1, the immunoreactions are considered to be in the kinetic regime, and hence incubations in this time scale will result in fluorescent signals linearly proportional to amount of expressed antigen on the tissue slices. Next, the rate of SBR increase is maximum until n=1 and start decreasing when the tissue slices were subjected to longer incubation times and, therefore, SBR per incubation time is kept at max when n=1 is used. (FIG. 9 (c)). We can conclude that the protocol with n=1 is the optimum, since it is the one in which the immunoreactions are in the kinetic regime with maximum SBR gain and also minimum achievable CV in signal level. That immediately translates into 4½ minutes of total protocol time.

To make a quantitative technical performance comparison with previous IHC techniques we designed a figure of merit, which is defined as the stained area per reagent volume, analysis time and reagent cost. Table 4 tabulates the results, which indicates nearly 100-fold improvement in time and 1000-fold overall improvement with respect to conventional techniques.

In an attempt to decrease the overall time spent per target, we have also questioned the feasibility of a multiplex protocol. Mixtures of primary antibodies and secondary antibodies are used to target more than one receptor, which in turn decreases the total time per target in the IHC assay. Table 2 shows the timing of such a protocol, which is applied to our breast cancer tissue slices. While having the same total time, the time per target has been reduced to half of the non-multiplexed protocol. FIG. 10 shows an example multiplex fluorescent detection of breast cancer biomarkers human epidermal growth factor receptor (HER2/neu) and Estrogen Receptor (ER) using immunohistochemistry with our system. Multiplex fluorescent detection of breast cancer biomarkers human epidermal growth factor receptor (HER2/neu) and Estrogen Receptor (ER) using immunohistochemistry with Microfluidic Tissue Processor. The detection was done with the optimized protocol having incubation time 2 min (n=1) and using a mixture of primary and secondary antibodies targeted against respective antigens. (a) The blue channel stands for nuclear counterstain conjugated with DAPI and helps to visualize the nucleus of the cells. (b) HER2/neu was detected with monoclonal rabbit anti-human primary antibody and visualized with Alexa-Fluor 594 labelled goat-anti-rabbit polyclonal IgG secondary antibody, represented here in the red channel. (c) Estrogen receptor (ER) was detected with monoclonal mouse anti-human primary antibody (Clone 6F11) and visualized with Alexa-Fluor 647 conjugated goat anti-mouse polyclonal IgG secondary antibody, represented here with green channel. (d) Shows three channels together. The width of the images corresponds to 600 μm and obtained by 6 by 6 stitching high-resolution images using a scanning fluorescent microscope.

Clinical Studies

In order to test the developed MTP system in a real-world setting, we have performed a series of immunohistochemical reactions on a set of 76 invasive ductal breast carcinomas retrieved from the archives of the institute of pathology. After the optimal experimental conditions for HER2/neu immunohistochemistry on MTP had been established, with incubation times for primary and secondary antibodies of 2 min (n=1), we applied our protocol to the 76 invasive ductal breast carcinomas. Comparison of diagnostic outcomes between conventional IHC and MTP-IHC is shown in FIG. 11. MTP-IHC produces 90% less ambiguous outcomes when compared with conventional IHC, and accurately predicts ISH amplification results. The inset table shows the cross-correlation of the conventional IHC and MTP-IHC scores for the 76 cases studied. Using MTP-IHC technique, we have not produced a single false-positive or false-negative result for the score (0) and (+) cases and the score (+++) cases, respectively. More importantly, the number of score (++) ambiguous cases was significantly reduced, from 27 cases to 3 cases (a reduction by almost 90%). 24 of the score (++) ambiguous cases that were diagnosed by classical IHC were either scored (0)/+ or (+++) by MTP-IHC, and in each of these 24 cases, the assignment corresponded to the gene amplification status. One case that had initially been diagnosed as (+++) case was reassigned a (++) score. Therefore, the eventual diagnostic HER2/neu outcome is much more accurately predicted when represented MTP-IHC is used instead of conventional IHC.

Alternative and Extended Areas of Use

Fluidic operation of the present invention is not only limited to generation of a pressure-driven flow. The inventive steps of the present device (simultaneous reduction of incubation time, keeping protocol reactions in the kinetic regime, leading to the demonstrated proportionality between the resultant read-out signal and the target antigen amount, and a high uniformity thanks to the fast and uniform exchange of fluids) do also apply when the fluid flow is induced by other actuation mechanisms, including but not limited to electrokinetic flow or thermally induced flow. For example, other inventions that employ electrokinetic or thermally induced flow exist (WO/2011/102801 and EP 1 974 814), however, in these documents the inventive step lies at certain arrangements (or designs, shapes, etc.) of specific electrodes that induce the flow itself. Such previous claims, therefore, cannot limit the use of the present invention when combined with other techniques to induce fluid flow inside the said microchannels and said the tissue chamber.

Similarly, the inventive steps of the present device also apply when a temperature control system, not limited to but preferably done by integrated (metal or polymer) electrodes and sensors and/or by taking into contact to a pre-heated element, is combined within the microfluidic device and the integrated system described in the present invention. For example, there exist other inventions that employ integrated and/or added temperature control systems (US/2005/009101) in a microfluidic system, however, in these documents the inventive step lies at certain characteristics, design and/or shape of heating and sensing elements that the temperature control system is composed of. Such previous claims, therefore, do not limit the use of the present invention when combined with a technique to realize temperature control within the said microchannels and the said tissue chamber.

An example application that requires temperature control is direct processing of the formalin-fixed paraffin embedded (FFPE) tissue sections. Processing of FFPE tissue sections requires paraffin wax removal (de-waxing), rehydration and antigen retrieval steps to be done on-chip. In fact, this is possible if micro-heaters (electrodes) can be made on the device, since antigen retrieval procedure generally needs heating of tissues at around 95° C. We can estimate the time required to realize this on-chip sample preprocessing based on the known time required for the staining protocol. Table 3 summarizes an on-chip dewaxing and antigen retrieval protocol, suggesting that such preprocessing is feasible in an additional period of 5 minutes. Therefore, together with the 2.5 minutes required for staining, the device has the potential to realize complete processing of FFPE tissue sections in 7.5 minutes, whereas the fastest reported complete processing until now is "the wave" mechanism (PCT/US2006/015020 and WO/2006/116037), having protocol time of 70 minutes.

Similarly, the inventive steps of the present device also apply when an imaging system (not limited to but preferably including light detectors or sources, or an array of light detectors, which can be fabricated using silicon microelectronics technology) for imaging of entities immobilized within the chamber is combined with the microfluidic device and the integrated system described in the present invention. For example, there exist other inventions that employ such imaging systems (WO/2010/148252) in a microfluidic context, however, in these documents the inventive step lies at certain characteristics, design and/or shape of these elements and/or structures that the imaging systems are composed of. Such previous claims, therefore, do not limit the use of the present invention in combination with a technique to integrate an imaging system within the microchannels and the tissue chamber.

Similarly, the inventive steps of the present device also apply when optical components (not limited to but preferably including lenses, objectives, microlens arrays, polarization and/or fluorescent light filters, located in front of light detectors and sources or array of these light detectors and sources) are combined with the microfluidic device and integrated system described in the present invention. For example, there exist many other inventions that employ such optical elements (WO/2010/148252) in a microfluidic context, however, in these documents the inventive step lies at certain characteristics, design and/or shape of these elements and/or structures that the optical systems are composed of. Such previous claims, therefore, do not limit the use of the present invention in combination with a technique to integrate optical elements within the microchannels and the tissue chamber.

The device described in the present invention proved to be useful for the immunohistochemical detection of cancer biomarkers, with much improved discriminative power in terms of the diagnostic outcome (as confirmed by gene amplification) when compared to conventional immunohistochemistry (FIG. 11). This is explained by the significantly shortened incubation time, allowing to profit from the proportionality that governs the initial first incubation minutes, where antibodies bind to antigens in a highly proportional fashion, with a constant binding rate as a direct function of antibody and antigen concentrations. Therefore, the application of the present invention is not limited to IHC, but can be used for any surface reaction that can be tuned to work in the proportional kinetic regime in order to achieve a reaction that is linearly proportional to the extent of the targets that are immobilized on a solid support.

The device described in the present invention makes use of an intelligent architectural arrangement of vertical access holes and a distributed microfluidic channel network around the periphery of the chamber (FIG. 3) and high pressure to guarantee a rapid, complete, and uniform bioreagent exchange within the low volume of the large (16 mm by 16 mm) but very shallow (less than 100 um) incubation chamber overlying the tissue slices (FIGS. 2-8). In this fashion, the wash-and-fill period of the bioreagents over the tissue slices due to the obtained convective flow is kept at an absolute minimum of 5-7 seconds, while no-flow conditions are assured during the actual incubation period. Besides, we observed that the increase of the SBR ratio as a function of incubation time is more prominent during the initial reaction-limited linear regime (FIG. 9 (c)), indicating that a short incubation time, in the present device, is in general sufficient to achieve sufficiently strong read-out signals without necessarily increasing detection antibody concentrations.

A 10 minute complete processing time from FFPE tissues also fits well with the time scale of the intra-operative utilization of the technique, as well as the use of a stand-alone miniaturized and automated diagnostic IHC system. Decreasing dead volumes, increasing the system pressure and realizing uniform reagent and buffer flows over the tissue samples, helped reducing the assay time, which is short enough to be considered as an immediate feedback during surgery. Tissue slices immobilized on standard glass slides are mechanically clamped to a microfluidic structure and can be replaced within one minute, which is the only assembly step needed to change the TS. The figure of merit comparison (Table 4) revealed that the present invention can demonstrate 1000-fold improvement when compared to existing techniques.

The presented technology can easily be transformed into a stand-alone, complete immunohistochemical diagnosis solution by integration of a miniaturized microscope. Therefore, the diagnosis can be done without additional infrastructure, trained personnel and virtually at no maintenance.

The present invention is however not limited to the examples discussed previously.

CITED REFERENCES

Vanesa Fernandez-Moreira, Bo Song, Venkataragavalu Sivagnanam, Anne-Sophie Chauvin, Caroline D. B. Vandevyver, Martin Gijs, Ilkka Hemmilä, Hans-Anton Lehr, and Jean-Claude G. Bünzli. Bioconjugated lanthanide luminescent helicates as multilabels for lab-on-a-chip detection of cancer biomarkers. *Analyst*, number 135, pages 42-52, 2010.B Ata Tuna Ciftlik, Bo Song, Caroline Vandevyver, Jean-Claude Bünzli, Hans-Anton Lehr, and Martinus Gijs. Fast immunohistochemical biomarker detection device for cancer tissue slices. Proceedings of 14*th International Conference on Miniaturized Systems for Chemistry and Life Sciences*, Groningen, Netherlands, October 3-7, 2010, 2010.

Minseok S. Kim, Seyong Kwon, Taemin Kim, Eun Sook Lee, Je-Kyun Park. Quantitative proteomic profiling of breast cancers using a multiplexed microfluidic platform for immunohistochemistry and immunocytochemistry, *Biomaterials*, Volume 32, Issue 5, February 2011, Pages 1396-1403

Kim M S, Kim T, Kong S-Y, Kwon S, Bae C Y, et al. Breast cancer diagnosis using a microfluidic multiplexed immunohistochemistry platform. *PLoS ONE* 5(5): e10441.doi: 10.1371/journal.pone.0010441, 2010

Page Erickson, Michael Everman, Michael Bell, Kevin Edberg, Matthew Botke. Enhanced fluidic method and apparatus for automated rapid immunohistochemistry. PCT/US2006/015020, WO/2006/116037, 2011

Micheal Mcneely, Nis Adey, Mark Spute, Edward Ayliffe, et. al., Method and system for microfluidic interfacing to array. PCT/US02/07113, WO/2002/072264, 2002

Arthur Queval, Nageswara R. Ghattamaneni, Cécile M. Perrault, Raminder Gill, Maryam Mirzaei, R. Anne McKinney and David Juncker. Chamber and microfluidic probe for microperfusion of organotypic brain slices. *Lab Chip*, 2010, 10, 326-334

Emmanuel Delamarche, Ute Dreschsler, and Robert Lovchik. Multilayer microfluidic probe head and method of fabrication thereof. PCT/I B2010/052018, WO/2010/128483, 2010

Emmanuel Delamarche, David Juncker, Bruno Michel, and Heinz Schmid. Method and device for flowing a liquid on a surface. PCT/IB2003/005350, WO/2004/050246, 2004

Lamprecht Waltraud, Mathes Anton, Wenczel Gyoergy, and Streit Wolfgang. Device and process unit for providing a hybridization chamber. US/2006/0003440, 2006

Jon Hoshizaki, Joon Mo Yang, Maryam Shariati, David Cox, Kirk Hirano et. al., Low-volume sequencing system and method of use. PCT/US2010/047392, WO 2011/026136, 2011

Nils Adey. Laminated microarray interface device. PCT/US02/24616, WO/2003/015922, 2003.

Gibum Kim, Todd Schwoerer. Microfluidic apparatus for wide area microfluidics. PCT/US2008/074865, WO/2009/029845, 2009

Ata Tuna Ciftlik and Martin A. M. Gijs, Parylene to silicon nitride bonding for post-integration of high pressure microfluidics to CMOS devices, *Lab on a Chip*, 2012, 12 (2), 396-400.doi:10.1039/c11c20727j.

Mark A Eddings, Michael A Johnson and Bruce K Gale, Determining the optimal PDMS-PDMS bonding technique for microfluidic devices, *Journal of Micromechanics and Microengineering*, 2008, 18, 067001.

Nathaniel Robinson and Per Erlandsson, An electrokinetic fluidic system, WO/2011/102801, 2011.

Koninklijke Philips Electronics NV, A microfluidic device based up on active matrix principles, EP1974814, 2008

Gary Blackburn, Microfluidic devices comprising biochannels, US/2005/009101, 2005.

Jody Vykoukal, Daynene M. Vykoukal, Gregory P. Stone, Eckhard U. Alt, method and apparatus for quantitative microimaging, WO/2010/148252, 2010.

The invention claimed is:

1. A biological and chemical sample processing device comprising a microfluidic device configured to receive a detachable slide containing samples, said microfluidic device comprising a sealing ring positioned on a bottom side of the microfluidic device, said sealing ring configured to seal a microfluidic chamber, said microfluidic chamber formed by the bottom side of the microfluidic device and the detachable slide brought into contact with the sealing ring prior to sample processing, a first and a second arrangement of microfluidic access holes located adjacent a side of the microfluidic chamber opposite the detachable slide and extending into the microfluidic chamber, the first arrangement of microfluidic access holes being configured for injecting fluid to said microfluidic chamber, the second arrangement of microfluidic access holes being configured for collecting fluid from said microfluidic chamber, wherein said microfluidic chamber forms a single chamber in fluid communication with a plurality of access holes of the first arrangement of microfluidic access holes and with a plurality of access holes of the second arrangement of microfluidic access holes, and wherein said first and second arrangements of microfluidic access holes are configured for advective transport of fluidic substances and reagents inside said microfluidic chamber, said microfluidic device further comprising inlet and outlet ports connected to microfluidic channels formed external to the microfluidic chamber, wherein the microfluidic channels are connected to the microfluidic access holes of said first and second arrangements, so as to form a distributed network channel on the top side of the microfluidic device, wherein the microfluidic channels form a distributed network such that the number of microfluidic access holes is greater than the number of inlets and outlets ports, the microfluidic channels extending essentially parallel to the bottom side of the microfluidic device, the microfluidic access holes and the inlet and outlet ports extending transversely to the bottom side of the microfluidic device.

2. The biological and chemical sample processing device according to claim 1, wherein said microfluidic chamber has a chamber height less than 100 µm.

3. The biological and chemical sample processing device according to claim 1, wherein said microfluidic access holes for in-flow and out-flow are located along edges of one said microfluidic chamber.

4. The biological and chemical sample processing device according to claim 3, wherein said microfluidic access holes comprise holes for in-flow arranged along an edge of the microfluidic chamber and holes for out-flow arranged along an opposite edge of the microfluidic chamber.

5. The biological and chemical sample processing device according to claim 1, wherein said distributed network channel is arranged on opposite sides of the microfluidic chamber.

6. The biological and chemical sample processing device according to claim 1, wherein said first arrangement of access holes is distributed along one edge of the microfluidic chamber and wherein the second arrangement of access holes is distributed along three other edges of one said microfluidic chamber.

7. The biological and chemical sample processing device according to claim 1, wherein the height of the microfluidic chamber is between 50 µm and 100 µm.

8. A method of biological and chemical sample processing, comprising steps of:
providing a biological and chemical sample processing device according to claim 1;
placing the detachable slide in contact with the sealing ring of the microfluidic device to form the microfluidic chamber;
injecting at least one reagent fluid into the microfluidic chamber via the inlet ports;

detecting a reaction of the sample to be tested with the reagent fluid.

9. The method according to claim 8 further comprising subjecting the sample to be tested to more than one fluid sequentially.

10. The method according to claim 8 wherein the sample to be tested is a biological sample.

11. The method according to claim 10 wherein the detection of the reaction of the biological sample with the reagent fluid comprises any one of
   i. a histochemical detection process
   ii. a cytochemical detection detection process
   iii. an immunohistochemical detection process
   iv. an immunocytochemical detection process
   v. an immunohistofluorescence detection process
   vi. an immunocytofluorescence detection process
   vii. an in situ hybridization detection process
   viii. a fluorescence in situ hybridization detection process
   ix. an antigen detection process
   x. an epitope detection process.

12. A biological and chemical sample processing device comprising a microfluidic device comprising a sealing ring positioned on a bottom side of the microfluidic device and configured to seal a microfluidic chamber facing said bottom side, a slide containing samples in contact with the sealing ring forming the microfluidic chamber, a first and a second arrangement of microfluidic access holes located adjacent a side of the microfluidic chamber opposite the slide and extending into the microfluidic chamber, the first arrangement of microfluidic access holes being configured for injecting fluid to the microfluidic chamber and collecting fluid from the microfluidic chamber, the second arrangement of microfluidic access holes being configured for collecting fluid from the microfluidic chamber, wherein said microfluidic chamber forms a single chamber in fluid communication with a plurality of access holes of the first arrangement of microfluidic access holes and with a plurality of access holes of the second arrangement of microfluidic access holes, and wherein said first and second arrangements of microfluidic access holes are configured for advective transport of fluidic substances and reagents inside said microfluidic chamber, said microfluidic device further comprising inlet and outlet ports connected to microfluidic channels formed external to the microfluidic chamber, wherein the microfluidic channels are connected to the microfluidic access holes of said first and second arrangements so as to form a distributed network channel on the top side of the microfluidic device, wherein the microfluidic channels form a distributed network suck that the number of microfluidic access holes is greater than the number of inlets and outlets ports, the microfluidic channels extending essentially parallel to the bottom side of the microfluidic device, the microfluidic access holes and the inlets and outlets ports extending transversely to the bottom side of the microfluidic device.

13. The biological and chemical sample processing device according to claim 12, wherein said distributed network channel is arranged on opposite sides of the microfluidic chamber.

14. The biological and chemical sample processing device according to claim 12, wherein said first arrangement of access holes is distributed along one edge of the microfluidic chamber and wherein the second arrangement of access holes is distributed along three other edges of said microfluidic chamber.

* * * * *